United States Patent [19]
Chang

[11] Patent Number: 5,955,480
[45] Date of Patent: Sep. 21, 1999

[54] TRIARYL SUBSTITUTED IMIDAZOLES, COMPOSITIONS CONTAINING SUCH COMPOUNDS AND METHODS OF USE

[75] Inventor: Linda L. Chang, Wayne, N.J.

[73] Assignee: Merck & Co., Inc., Rahway, N.J.

[21] Appl. No.: 08/972,021

[22] Filed: Nov. 17, 1997

Related U.S. Application Data

[60] Provisional application No. 60/031,467, Nov. 20, 1996.
[51] Int. Cl.$^6$ .................... C07D 401/04; A61K 31/44
[52] U.S. Cl. ........................ 514/341; 546/274.1
[58] Field of Search ................ 546/274.1; 514/341

[56] References Cited

U.S. PATENT DOCUMENTS

| | | | |
|---|---|---|---|
| 4,608,382 | 8/1986 | Ferrini et al. | 514/341 |
| 5,633,377 | 5/1997 | Thurkauf et al. | 544/370 |
| 5,656,644 | 8/1997 | Adams et al. | 514/341 |

*Primary Examiner*—Jane Fan
*Attorney, Agent, or Firm*—Mollie M. Yang; David L. Rose

[57] ABSTRACT

2,4-Diaryl-5-pyridylimidazoles are glucagon antagonists and inhibitors of the biosynthesis and/or action of TNF-α and IL-1. The compounds block the action of glucagon at its receptor and thereby decrease the levels of plasma glucose. The instant imidazoles are also inhibitors of TNF-α and IL-1. Compounds of the present invention may be used for glucagon-mediated as well as cytokine mediated diseases. Cytokine mediated diseases refers to diseases or conditions in which excessive or unregulated production of one or more cytokines occurs. Interleukin-1 (IL-1) and Tumor Necrosis Factor (TNF) are cytokines produced by a variety of cells, which are involved in immunoregulation and other physiological conditions, such as inflammation.

10 Claims, No Drawings

TRIARYL SUBSTITUTED IMIDAZOLES, COMPOSITIONS CONTAINING SUCH COMPOUNDS AND METHODS OF USE

CROSS REFERENCE TO RELATED APPLICATIONS

This application is based on, and claims priority from, provisional application 60/031,467 filed on Nov. 20, 1996.

BACKGROUND OF THE INVENTION

The present invention relates to triaryl substituted imidazoles which antagonize the metabolic effect of glucagon and are inhibitors of the biosynthesis and/or action of cytokines including TNF-α and IL-1. This invention also relates to compositions containing such compounds and methods of treatment using such compounds.

Diabetes is a disease process derived from multiple causative factors and characterized by elevated levels of plasma glucose. Uncontrolled hyperglycemia is associated with an increased risk for microvascular and macrovascular diseases, including nephropathy, retinopathy, hypertension, stroke and heart disease. Control of glucose homeostasis is, therefore, a major approach to the treatment of diabetes. Glucagon is a major counter regulatory hormone that attenuates the inhibition of liver gluconeogenesis by insulin. Glucagon receptors are found primarily in the liver, although their presence has been documented in kidney, pancreas, adipose tissues, heart, smooth muscles of vascular tissues, and some regions of the brain, stomach and adrenal glands.

Type II diabetics have elevated levels of plasma glucagon and increased rates of hepatic glucose production. The rate of hepatic glucose production positively correlates with fasting blood glucose levels in type II diabetics. Therefore, antagonists of glucagon are useful in improving insulin responsiveness in the liver, decreasing the rate of gluconeogenesis and lowering the rate of hepatic glucose output resulting in a decrease in the levels of plasma glucose.

A monoclonal antibody to glucagon (Glu-mAb) has been utilized to test the acute effects of attenuation of glucagon action in streptozotocin-treated diabetic rats (Brand et al., Diabetologia 37:985, 1994). In contrast to a control antibody, injection of Glu-mnAb attenuated the postprandial increase in blood glucose in moderately hyperglycemic rats (i.e., rats with a moderate impairment in insulin secretion). In severely hyperglycemic rats (i.e., rats with severely impaired insulin secretion), Glu-mAb injection did not lower blood glucose levels, but potentiated the hypoglycemic effect of a suboptimal dose of insulin. These data suggest that attenuation of the action of glucagon in these models leads to increased sensitivity to the action of insulin, but does not lead to decreased blood glucose levels in the absence of insulin. On the other hand, a monoclonal antibody to glucagon was effective in lowering plasma glucose levels in diabetic rabbits independent of insulin effects (Brand et al., Diabetes, 45:1076 (1996). While these data support the notion that antagonism of glucagon action will provide beneficial therapy for both type I and type II diabetics, this hypothesis could be more rigorously tested if a specific non-peptidyl glucagon antagonist were available.

The regulation of glucagon homeostasis is also mediated by the hormone insulin, produced in the β cells of the pancreas. Deterioration of these cells is typically observed in Type I diabetics, and abnormalities in the function of these cells may occur in patients presenting the symptoms of Type II diabetes. Thus, a glucagon antagonist might have utility in treating Type I diabetics.

The glucagon receptor is expressed in kidney tissues where glucagon has been demonstrated to have an effect on electrolyte homeostasis including the ions sodium, potassium, chloride, magnesium, calcium, and phosphate and the non-electrolytes urea and water (Ahloulay et al., Am. J. Physiol., 269: F225, 1995). A glucagon antagonist may have use in treating disorders involving electrolyte imbalance. The kidney is also gluconeogenic in response to glucagon (Amores et al., Molec. Cell. Biochem., 137: 117, 1994) and an antagonist would act to lower glucose production in kidney furthering the treatment of diabetes.

Glucagon receptors are present in the heart and in smooth muscles. Glucagon has a direct effect on cardiac output and heart rate (Glick et al., Circ. Res., 22: 789 (1968); Farah, Pharm. Rev., 35: 181, 1983). A strong correlation has been observed in patients with hypertension and elevated plasma glucagon levels resulting from impaired hepatic catabolism (Silva et al., Heptatology, 11: 668, 1990). Antagonism of the effects of elevelated glucagon levels may have an effect on certain types of hypertension, thus a glucagon antagonist may have utility in the treatment of certain types of hypertension associated with elevated glucagon production.

The primary role for glucagon and glucagon receptors associated with adipose tissues is to induce lipolysis, thus providing free fatty acids as a substrate for fat burning tissues (Saggerson et al., Biochem. J., 238: 387, 1986). An antagonist to this effect might be useful in treating conditions where there is excessive lipolysis of fat stores resulting from elevated glucagon levels, such as wasting disease (cachexia).

Glucagon and glucagon receptors have been localized to the hippocampus region of the brain (Hoosein and Gurd, Proc. Natl. Acad. Sci. USA, 81: 4368, 1984). This discovery suggests that glucagon may have a neuroendocrine role in initiating or elaborating basic behavior or somatic motor programs. Since glucagon secretion is increased in response to low blood glucose levels, increased glucagon levels in the brain may initiate behavior to respond to low glucose levels, such as eating. Thus, chronic hyperglucagonemia may also result in a constant craving for food resulting in obesity. A glucagon antagonist may have utility in treating obesity by altering feeding behavior associated with a response to glucagon.

Cytokine mediated diseases refers to diseases or conditions in which excessive or unregulated production of one or more cytokines occurs. Interleukin-1 (IL-1), Interleukin-6 (IL-6), Interleukin-8 (IL-8) and Tumor Necrosis Factor (TNF) are cytokines produced by a variety of cells, which are involved in immunoregulation and other physiological conditions, such as inflammation.

IL-1 has been demonstrated to mediate a variety of biological activities thought to be important in immunoregulation and other physiological conditions. [See, e.g., Dinarello et al., Rev. Infect. Disease, 6, 51 (1984)]. The myriad of known biological activities of IL-1 include the activation of T-helper cells, induction of fever, stimulation of prostaglandin or collagenase production, neutrophil chemotaxis, induction of acute phase proteins and the suppression of plasma iron levels.

There are many disease states in which IL-1 is implicated. Included among these diseases are rheumatoid arthritis, osteoarthritis, endotoxemia, toxic shock syndrome, other acute or chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis. Recent evidence also links IL-1 activity to diabetes and pancreatic β cells.

IL-6 is a cytokine affecting the immune system, hematopoiesis and acute phase reactions. It is produced by several mammalian cell types in response to agents such as IL-1 and is correlated with disease states such as angiofollicular lymphoid hyperplasia.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, fibroblasts, and endothelial cells. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils. It causes lysozomal enzyme release and respiratory burst from neutrophils, and it has been shown to increase the surface expression of Mac-1 (CD11b/CD 18) on neutrophils without de novo protein synthesis. The compounds of formula I are also useful in treating diseases characterized by excessive IL-8 activity. There are many disease states in which excessive or unregulated IL-8 production is implicated in exacerbating and/or causing the disease. These diseases include psoriasis, inflammatory bowel disease, asthma, cardiac and renal reperfusion injury, adult respiratory distress syndrome, thrombosis and glomerulonephritis.

Excessive or unregulated TNF production has been implicated in mediating or exacerbating rheumatoid arthritis, rheumatoid spondylitis, osteoarthritis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host reaction, allograft rejections, fever and myalgias due to infection, such as influenza, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Cytokines, such as TNF, have been shown to activate HIV replication in monocytes and/or macrophages [See Poli, et al., Proc. Natl. Acad. Sci., 87: 782–784 (1990)]. Therefore, inhibition of monokine production or activity aids in limiting HIV progression as stated above for T-cells. TNF has also been implicated in various roles with other viral infections, such as the cytomegalovirus (CMV), influenza virus and the herpes virus.

There remains a need for treatment, in this field, for compounds which are cytokine suppressive or antagonistic, i.e., compounds which are capable of interfering with, inhibiting or antagonizing cytokines such as IL-1, IL-6, IL-8 and TNF.

The compounds in the present invention are glucagon antagonists and inhibitors of the biosynthesis and action of IL-1, IL-6, IL-8 and TNF. The compounds block the action of glucagon at its receptors and thereby decrease the levels of plasma glucose. The instant compounds thus are useful as antidiabetic agents. Glucagon may have other direct effects on cardiac output, lipolysis, and feeding behavior and therefore may be useful as antihypertensive, anti-cachexia or antiobesity agents. Compounds of the present invention are also useful for the treatment of cytokine mediated diseases.

SUMMARY OF THE INVENTION

The present invention relates to 2,4-diaryl-5-pyridyl imidazoles which are glucagon receptor antagonists as well as cytokine inhibitors. These compounds are therefore useful for the treatment of diseases mediated by glucagon as well diseases mediated by cytokines. Diseases caused by excessive levels of glucagon, include diabetes and certain types of hypertension, cachexia and obesity. Cytokine-mediated diseases are for example rheumatoid arthritis, osteoarthritis, endotoxemia, toxic shock syndrome, other acute or chronic inflammatory diseases, such as the inflammatory reaction induced by endotoxin or inflammatory bowel disease (Crohn's disease, ulcerative colitis), tuberculosis, atherosclerosis, muscle degeneration, cachexia, psoriatic arthritis, Reiter's syndrome, rheumatoid arthritis, gout, traumatic arthritis, rubella arthritis and acute synovitis, angiofollicular lymphoid hyperplasia, psoriasis, inflammatory bowel disease, asthma, cardiac and renal reperfusion injury, adult respiratory distress syndrome, thrombosis and glomerulonephritis, rheumatoid spondylitis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host reaction, allograft rejections, fever and myalgias due to infection, such as influenza, keloid formation, scar tissue formation and pyresis.

Also included in the invention are pharmaceutical compositions which comprise a compound of formula I in combination with a pharmaceutically acceptable carrier.

Also included in the invention are methods of treating glucagon mediated disease, comprising administering to a mammalian patient in need of such treatment an amount of a compound of formula I which is effective to treat said disease.

Also included in the invention are methods of treating cytokine mediated disease in a mammal, comprising administering to a mammalian patient in need of such treatment an amount of a compound of formula I which is effective to treat said cytokine mediated disease.

DETAILED DESCRIPTION OF THE INVENTION

The present invention provides compounds of formula (I):

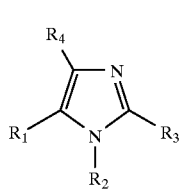

(I)

wherein
$R_1$ is 4-pyridyl, 4-pyrimidinyl, 4-quinolyl or pyridazinyl, each of which is unsubstituted or substituted with one or two substituents each of which is independently selected from the group consisting of
(1) halogen,
(2) —CN, (3) $C_{1-10}$ alkyl, wherein said alkyl is optionally substituted with from 1 to 5 halogen atoms,
(4) —O—$C_{1-10}$ alkyl,
(5) —S—$C_{1-10}$ alkyl,
(6) —$NR_8R_9$, and
(7) —$NO_2$;

$R_2$ is hydrogen, —$C(Z)OC_{1-4}$ alkyl, —$C(Z)C_{1-4}$ alkyl, or —$S(O)_2C_{1-4}$ alkyl; $R_3$ is phenyl, 1-naphthyl, 2-naphthyl or heteroaryl each of which is unsubstituted or substituted with one, two or three substituents each of which is independently selected from the group consisting of
(1) $C_{1-10}$ alkyl,
(2) $R_5$, and
(3) $C_{1-10}$ alkyl substituted with up to 5 groups independently selected from $R_5$;

$R_4$ is —X—Ar wherein
X is a bond and Ar is substituted phenyl, substituted 1-naphthyl, or substituted 2-naphthyl, wherein said substituent is one or two groups each of which is independently selected from the group consisting of
(1) phenyl, optionally substituted with up to 5 groups independently selected from $C_{1-10}$ alkyl, $R_5$, and $C_{1-10}$ alkyl substituted with up to 5 groups independently selected from $R_5$,
(2) 1-naphthyl, optionally substituted with up to 5 groups independently selected from $C_{1-10}$ alkyl, $R_5$, and $C_{1-10}$ alkyl substituted with up to 5 groups independently selected from $R_5$,
(3) 2-naphthyl, optionally substituted with up to 5 groups independently selected from $C_{1-10}$ alkyl, $R_5$, and $C_{1-10}$ alkyl substituted with up to 5 groups independently selected from $R_5$,
(4) heteroaryl, optionally substituted with up to 5 groups independently selected from $C_{1-10}$ alkyl, $R_5$, and $C_{1-10}$ alkyl substituted with up to 5 groups independently selected from $R_5$, X is —$C_{1-4}$ alkyl-, —C(Z)—, or —$C(Z)C_{1-4}$ alkyl- where —C(Z) is the point of attachment to the imidazole ring, and Ar is phenyl, 1-naphthyl, 2-naphthyl, or heteroaryl, and Ar is unsubstituted or substituted with one, two, or three substituents each of which is independently selected from the group consisting of
(1) $C_{1-10}$ alkyl,
(2) $R_5$,
(3) $C_{1-10}$ alkyl substituted with up to 5 groups independently selected from $R_5$,
(4) phenyl, optionally substituted with up to 5 groups independently selected from $C_{1-10}$ alkyl, $R_5$, and $C_{1-10}$ alkyl substituted with up to 5 groups independently selected from $R_5$,
(5) 1-naphthyl, optionally substituted with up to 5 groups independently selected from $C_{1-10}$ alkyl, $R_5$, and $C_{1-10}$ alkyl substituted with up to 5 groups independently selected from $R_5$,
(6) 2-naphthyl, optionally substituted with up to 5 groups independently selected from $C_{1-10}$ alkyl, $R_5$, and $C_{1-10}$ alkyl substituted with up to 5 groups independently selected from $R_5$,
(7) heteroaryl, optionally substituted with up to 5 groups independently selected from $C_{1-10}$ alkyl, $R_5$, and $C_{1-10}$ alkyl substituted with up to 5 groups independently selected from $R_5$, $R_5$ is
(1) —$OR_8$,
(2) —$NO_2$,
(3) halogen
(4) —$S(O)_mR_{11}$,
(5) —$SR_8$,
(6) —$S(O)_mOR_8$,
(7) —$S(O)_mNR_8R_9$,
(8) —$NR_8R_9$,
(9) —$O(CR_{10}R_{20})_pNR_8R_9$,
(10) —$C(O)R_8$,
(11) —$CO_2R_8$,
(12) —$CO_2(CR_{10}R_{20})_nCONR_8R_9$,
(13) —$ZC(O)R_8$,
(14) —CN,
(15) —$C(Z)NR_8R_9$,
(16) $NR_{10}C(Z)R_8$,
(17) —$C(Z)NR_8OR_9$,
(18) $NR_{10}C(Z)NR_8R_9$,
(19) —$NR_{10}S(O)_mR_{11}$,
(20) —$C(=NOR_{21})R_8$,
(21) —$NR_{10}C(=NR_{15})SR_{11}$,
(22) —$NR_{10}C(=NR_{15})NR_8R_9$,
(23) —$NR_{10}C(=CR_{14}R_{24})SR_{11}$,
(24) —$NR_{10}C(=CR_{14}R_{24})NR_8R_9$,
(25) —$NR_{10}C(O)C(O)NR_8R_9$,
(26) —$NR_{10}C(O)C(O)OR_{10}$,
(27) —$C(=NR_{13})NR_8R_9$,
(28) —$C(=NOR_{13})NR_8R_9$,
(29) —$C(=NR_{13})ZR_{11}$,
(30) —$OC(Z)NR_8R_9$,
(31) —$NR_{10}S(O)_mCF_3$,
(32) —$NR_{10}C(Z)OR_{10}$,
(33) 5-($R_{18}$)-1,2,4-oxadiazol-3-yl,
(34) 4-($R_{12}$)-5-($R_{18}R_{19}$)-4,5-dihydro-1,2,4-oxadiazol-3-yl;

$R_8$ and $R_9$ are independently selected from
(1) hydrogen,
(2) heterocyclyl,
(3) heterocyclylalkyl, and
(4) $R_{11}$; or $R_8$ and $R_9$ together with the nitrogen to which they are attached form a heterocyclic ring of 5 to 7 members which ring optionally contains an additional heteroatom selected from oxygen, sulfur or $NR_{12}$;

$R_{10}$ and $R_{20}$ is each independently selected from hydrogen and $C_{1-4}$ alkyl;

$R_{11}$ is
(1) $C_{1-10}$ alkyl,
(2) halo-substituted $C_{1-10}$ alkyl,
(3) $C_{2-10}$ alkenyl,
(4) $C_{2-10}$ alkynyl,
(5) $C_{3-7}$ cycloalkyl,
(6) $C_{5-7}$ cycloalkenyl,
(7) aryl, optionally substituted with $OR_{10}$,
(8) arylalkyl, wherein the aryl portion is optionally substituted with $OR_{10}$,
(9) heteroaryl or
(10) heteroarylalkyl;

$R_{12}$ is (1) hydrogen,
(2) —C(Z)R$_{13}$,
(3) optionally substituted C$_{1-4}$ alkyl, wherein the substituents may be halo, C$_{1-3}$ alkoxy, amino, or carboxy,
(4) optionally substituted aryl C$_{1-4}$ alkyl, wherein the substituents may be halo, C$_{1-3}$ alkoxy, amino, or carboxy, or
(5) S(O)$_2$R$_{25}$;

R$_{13}$ is
(1) hydrogen, or
(2) R$_{25}$;

R$_{14}$ and R$_{24}$ is each independently selected from
(1) hydrogen,
(2) C$_{1-4}$ alkyl,
(3) nitro and
(4) cyano;

R$_{15}$ is
(1) hydrogen,
(2) cyano,
(3) C$_{1-4}$ alkyl,
(4) C$_{3-7}$ cycloalkyl or
(5) aryl;

R$_{18}$ and R$_{19}$ are independently selected from
(1) hydrogen,
(2) C$_{1-4}$ alkyl,
(3) substituted alkyl, wherein the substituents may be halo, C$_{1-3}$ alkoxy, amino, or carboxy,
(4) optionally substituted aryl, wherein the substituents may be halo, C$_{1-3}$ alkoxy, amino, or carboxy, and
(5) optionally substituted arylalkyl, wherein the substituents may be halo, C$_{1-3}$ alkoxy, amino, or carboxy;

R$_{18}$ and R$_{19}$ together denote an oxo or thioxo;

R$_{21}$ is
(1) R$_{13}$,
(2) a pharmaceutically acceptable cation, or
(3) aroyl, or
(4) C$_{1-10}$ alkanoyl;

R$_{25}$ is
(1) C$_{1-1}$ alkyl,
(2) C$_{3-7}$ cycloalkyl,
(3) heterocyclyl,
(4) aryl,
(5) aryl C$_{1-10}$ alkyl,
(6) heterocyclyl-C$_{1-10}$ alkyl,
(7) heteroaryl or
(8) heteroaryl C$_{1-10}$ alkyl;

Z is oxygen or sulfur;
m is 1 or 2;
n is 1 to 10;
p is 1 to 10;
a pharmaceutically acceptable salt thereof.

In one subset of the present compounds, there are provided compounds of formula (I) wherein
R$_1$ is 4-pyridyl which is unsubstituted or substituted with one or two substituents each of which is independently selected from the group consisting of
(1) halogen,
(2) —CN,
(3) C$_{1-10}$ alkyl, wherein said alkyl is optionally substituted with from 1 to 5 halogen atoms,
(4) —O—C$_{1-10}$ alkyl,
(5) —S—C$_{1-10}$ alkyl,
(6) —NR$_8$R$_9$, and
(7) —NO$_2$.

Another subset of the present compounds provides compounds of formula (I) wherein R$_2$ is H or —C(Z)OC$_{1-4}$ alkyl, and Z is oxygen or sulfur.

In a further subset of the present compounds, there are provided compounds of formula (I) wherein
R$_3$ is phenyl, 1-naphthyl or 2-naphthyl each of which is unsubstituted or substituted with one, two or three groups each of which is independently selected from the group consisting of
(1) C$_{1-10}$ alkyl,
(2) R$_5$, and
(3) C$_{1-10}$ alkyl substituted with up to 5 groups independently selected from R$_5$.

In another subset of the present invention, there are provided compounds of formula (I) wherein
R$_4$ is —X—Ar wherein
X is a bond and Ar is substituted phenyl, substituted 1-naphthyl, or substituted 2-naphthyl, wherein said substituent is one or two groups each of which is independently selected from the group consisting of
(1) phenyl, optionally substituted with up to 5 groups independently selected from C$_{1-10}$ alkyl, R$_5$, and C$_{1-10}$ alkyl substituted with up to 5 groups independently selected from R$_5$,
(2) 1-naphthyl, optionally substituted with up to 5 groups independently selected from C$_{1-10}$ alkyl, R$_5$, and C$_{1-10}$ alkyl substituted with up to 5 groups independently selected from R$_5$,
(3) 2-naphthyl, optionally substituted with up to 5 groups independently selected from C$_{1-10}$ alkyl, R$_5$, and C$_{1-10}$ alkyl substituted with up to 5 groups independently selected from R$_5$,
(4) heteroaryl, optionally substituted with up to 5 groups independently selected from C$_{1-10}$ alkyl, R$_5$, and C$_{1-10}$ alkyl substituted with up to 5 groups independently selected from R$_5$, or X is C$_{1-4}$ alkyl or —C(Z)— and Ar is phenyl, 1-naphthyl, 2-naphthyl, or heteroaryl, and Ar is unsubstituted or substituted with one, two, or three substituents each of which is independently selected from the group consisting of
(1) C$_{1-10}$ alkyl,
(2) R$_5$,
(3) C$_{1-10}$ alkyl substituted with up to 5 groups independently selected from R$_5$,
(4) phenyl, optionally substituted with up to 5 groups independently selected from C$_{1-10}$ alkyl, R$_5$, and C$_{1-10}$ alkyl substituted with up to 5 groups independently selected from R$_5$,
(5) 1-naphthyl, optionally substituted with up to 5 groups independently selected from C$_{1-10}$ alkyl, R$_5$, and C$_{1-10}$ alkyl substituted with up to 5 groups independently selected from R$_5$,
(6) 2-naphthyl, optionally substituted with up to 5 groups independently selected from C$_{1-10}$ alkyl, R$_5$, and C$_{1-10}$ alkyl substituted with up to 5 groups independently selected from R$_5$,
(7) heteroaryl, optionally substituted with up to 5 groups independently selected from C$_{1-10}$ alkyl, R$_5$, and C$_{1-10}$ alkyl substituted with up to 5 groups independently selected from R$_5$.

In a preferred embodiment of the present invention there are provided compounds of formula (I) wherein
$R_1$ is 4-pyridyl, 4-pyrimidinyl or 4-quinolyl;
$R_2$ is hydrogen or —C(Z)OC$_{1-4}$ alkyl;
$R_3$ is phenyl, 1-naphthyl, 2-naphthyl or heteroaryl each of which is unsubstituted or substituted with one, two or three substituents each of which is independently selected from the group consisting of
(1) $C_{1-10}$ alkyl,
(2) $R_5$, and
(3) $C_{1-10}$ alkyl substituted with up to 5 groups independently selected from $R_5$;
$R_4$ is —X—Ar wherein
X is a bond and Ar is substituted phenyl, substituted 1-naphthyl, or substituted 2-naphthyl, wherein said substituent is one or two groups each of which is independently selected from the group consisting of
  (1) phenyl, optionally substituted with up to 5 groups independently selected from $C_{1-10}$ alkyl, $R_5$, and $C_{1-10}$ alkyl substituted with up to 5 groups independently selected from $R_5$,
  (2) 1-naphthyl, optionally substituted with up to 5 groups independently selected from $C_{1-10}$ alkyl, $R_5$, and $C_{1-10}$ alkyl substituted with up to 5 groups independently selected from $R_5$,
  (3) 2-naphthyl, optionally substituted with up to 5 groups independently selected from $C_{1-10}$ alkyl, $R_5$, and $C_{1-10}$ alkyl substituted with up to 5 groups independently selected from $R_5$,
  (4) heteroaryl, optionally substituted with up to 5 groups independently selected from $C_{1-10}$ alkyl, $R_5$, and $C_{1-10}$ alkyl substituted with up to 5 groups independently selected from $R_5$, or
X is —CH$_2$— or —C(Z)—, and Ar is phenyl, 1-naphthyl, 2-naphthyl, or heteroaryl, and Ar is unsubstituted or substituted with one, two, or three substituents each of which is independently selected from the group consisting of
  (1) $C_{1-10}$ alkyl,
  (2) $R_5$,
  (3) $C_{1-10}$ alkyl substituted with up to 5 groups independently selected from $R_5$,
  (4) phenyl, optionally substituted with up to 5 groups independently selected from $C_{1-10}$ alkyl, $R_5$, and $C_{1-10}$ alkyl substituted with up to 5 groups independently selected from $R_5$,
  (5) 1-naphthyl, optionally substituted with up to 5 groups independently selected from $C_{1-10}$ alkyl, $R_5$, and $C_{1-10}$ alkyl substituted with up to 5 groups independently selected from $R_5$,
  (6) 2-naphthyl, optionally substituted with up to 5 groups independently selected from $C_{1-10}$ alkyl, $R_5$, and $C_{1-10}$ alkyl substituted with up to 5 groups independently selected from $R_5$,
  (7) heteroaryl, optionally substituted with up to 5 groups independently selected from $C_{1-10}$ alkyl, $R_5$, and $C_{1-10}$ alkyl substituted with up to 5 groups independently selected from $R_5$,
$R_5$ is
  (1) —OR$_8$,
  (2) halogen
  (3) —SR$_8$, or
$R_8$ is selected from
  (1) hydrogen,
  (2) $R_{11}$;
$R_{10}$ and $R_{20}$ is each independently selected from hydrogen and $C_{1-4}$ alkyl;
$R_{11}$ is
  (1) $C_{1-10}$ alkyl,
  (2) halo-substituted $C_{1-10}$ alkyl,
  (3) $C_{3-7}$ cycloalkyl,
  (4) aryl, optionally substituted with OR$_{10}$, or
  (5) arylalkyl, wherein the aryl portion is optionally substituted with OR$_{10}$;
Z is oxygen or sulfur;
a pharmaceutically acceptable salt thereof.

In a further preferred embodiment, there are provided compounds of formula (I) wherein
$R_1$ is 4-pyridyl;
$R_2$ is hydrogen or —C(Z)OC$_{1-4}$ alkyl;
$R_3$ is phenyl, 1-naphthyl or 2-naphthyl each of which is unsubstituted or substituted with one, two or three substituents each of which is independently selected from the group consisting of
  (1) halogen, and
  (2) OR$_8$;
$R_4$ is —X—Ar wherein
X is a bond and Ar is substituted phenyl, substituted 1-naphthyl, or substituted 2-naphthyl, wherein said substituent is one or two groups each of which is independently selected from the group consisting of
  (1) phenyl, optionally substituted with up to 5 groups independently selected from $C_{1-10}$ alkyl, $R_5$, and $C_{1-10}$ alkyl substituted with up to 5 groups independently selected from $R_5$,
  (2) 1-naphthyl, optionally substituted with up to 5 groups independently selected from $C_{1-10}$ alkyl, $R_5$, and $C_{1-10}$ alkyl substituted with up to 5 groups independently selected from $R_5$,
  (3) 2-naphthyl, optionally substituted with up to 5 groups independently selected from $C_{1-10}$ alkyl, $R_5$, and $C_{1-10}$ alkyl substituted with up to 5 groups independently selected from $R_5$,
  (4) heteroaryl, optionally substituted with up to 5 groups independently selected from $C_{1-10}$ alkyl, $R_5$, and $C_{1-10}$ alkyl substituted with up to 5 groups independently selected from $R_5$;
X is —CH$_2$— or —C(Z)—, and Ar is phenyl, 1-naphthyl, 2-naphthyl, or heteroaryl, and Ar is unsubstituted or substituted with one, two, or three substituents each of which is independently selected from the group consisting of
  (1) $C_{1-10}$ alkyl,
  (2) $R_5$,
  (3) $C_{1-10}$ alkyl substituted with up to 5 groups independently selected from $R_5$,
  (4) phenyl, optionally substituted with up to 5 groups independently selected from $C_{1-10}$ alkyl, $R_5$, and $C_{1-10}$ alkyl substituted with up to 5 groups independently selected from $R_5$,
  (5) 1-naphthyl, optionally substituted with up to 5 groups independently selected from $C_{1-10}$ alkyl, $R_5$, and $C_{1-10}$ alkyl substituted with up to 5 groups independently selected from $R_5$,
  (6) 2-naphthyl, optionally substituted with up to 5 groups independently selected from $C_{1-10}$ alkyl, $R_5$, and $C_{1-10}$ alkyl substituted with up to 5 groups independently selected from $R_5$, (7) heteroaryl, optionally substituted with up to 5 groups independently selected from $C_{1-10}$ alkyl, $R_5$, and $C_{1-10}$ alkyl substituted with up to 5 groups independently selected from $R_5$, $R_5$ is
(1) —$OR_8$,
(2) halogen, or
(3) —$SR_8$;

$R_8$ is selected from
(1) hydrogen,
(2) $R_{11}$;

$R_{10}$ and $R_{20}$ is each independently selected from hydrogen and $C_{1-4}$ alkyl;

$R_{11}$ is
(1) $C_{1-10}$ alkyl,
(2) halo-substituted $C_{1-10}$ alkyl,
(3) $C_{3-7}$ cycloalkyl,
(4) aryl, optionally substituted with $OR_{10}$, or
(5) arylalkyl, wherein the aryl portion is optionally substituted with $OR_{10}$;

Z is oxygen or sulfur;
a pharmaceutically acceptable salt thereof.

Especially preferred compounds of formula I include:
(1) 1-(t-butyloxycarbonyl)-4-(4-fluorophenyl)-2-(4-phenoxyphenyl)-5-(4-pyridyl)imidazole,
(2) 1-(ethoxycarbonyl)-5-(4-fluorophenyl)-2-(4-phenoxyphenyl)-4-(4-pyridyl)imidazole,
(3) 4-(4-biphenyl)-2-(4-chlorophenyl)-5-(4-pyridyl)imidazole,
(4) 4-(4-biphenyl)-2-(3-chlorophenyl)-5-(4-pyridyl)imidazole,
(5) 2-(4-chlorophenyl)-4-(4'-ethyl-4-biphenyl)-5-(4-pyridyl)imidazole,
(6) 2-(3-chlorophenyl)-4-(4'-ethyl-4-biphenyl)-5-(4-pyridyl)imidazole,
(7) 2-(4-chlorophenyl)-4-(4-(1-naphthyl)phenyl)-5-(4-pyridyl)imidazole,
(8) 2-(4-chlorophenyl)-4-(3'-methoxy-4-biphenyl)-5-(4-pyridyl)imidazole,
(9) 2-(4-chlorophenyl)-4-(4'-methoxy-4-biphenyl)-5-(4-pyridyl)imidazole,
(10) 2-(4-chlorophenyl)-4-(2'-methoxy-4-biphenyl)-5-(4-pyridyl)imidazole,
(11) 2-(4-chlorophenyl)-5-(4-pyridyl)-4-(4-(2-thienyl)phenyl)imidazole,
(12) 2-(4-chlorophenyl)-4-(4'-methoxy-3-biphenyl)-5-(4-pyridyl)imidazole,
(13) 2-(4-chlorophenyl)-4-(3'-methoxy-3-biphenyl)-5-(4-pyridyl)imidazole,
(14) 2-(4-chlorophenyl)-4-(4'-(4-methoxybenzylthio)-4-biphenyl)-5-(4-pyridyl)imidazole,
(15) 4-(3-biphenyl)-2-(4-chlorophenyl)-5-(4-pyridyl)imidazole,
(16) 2-(4-chlorophenyl)-4-(2'-methoxy-3-biphenyl)-5-(4-pyridyl)imidazole,
(17) 2-(4-chlorophenyl)-4-(3-(1-naphthyl)phenyl)-5-(4-pyridyl)imidazole,
(18) 2-(4-chlorophenyl)-4-(2',4'-dichloro-3-biphenyl)-5-(4-pyridyl)imidazole,
(19) 2-(4-chlorophenyl)-4-(3-(2-naphthyl)phenyl)-5-(4-pyridyl)imidazole,
(20) 2-(4-chlorophenyl)-4-(4'-chloro-3-biphenyl)-5-(4-pyridyl)imidazole,
(21) 2-(4-chlorophenyl)-4-(3'-chloro-3-biphenyl)-5-(4-pyridyl)imidazole,
(22) 2-(4-chlorophenyl)-4-(3',5'-dichloro-3-biphenyl)-5-(4-pyridyl)imidazole,
(23) 2-(4-chlorophenyl)-4-(4'-(4-methoxybenzylthio)-3-biphenyl)-5-(4-pyridyl)imidazole,
(24) 2-(4-chlorophenyl)-4-(3-(2-thienyl)phenyl)-5-(4-pyridyl)imidazole,
(25) 2-(4-chlorophenyl)-4-(3-(3-thienyl)phenyl)-5-(4-pyridyl)imidazole,
(26) 2-(4-chlorophenyl)-4-(2',4-dimethoxy-3-biphenyl)-5-(4-pyridyl)imidazole,
(27) 2-(4-chlorophenyl)-4-benzyl-5-(4-pyridyl)imidazole,
(28) 2-(4-chlorophenyl)-4-(2-biphenyl)methyl-5-(4-pyridyl)imidazole,
(29) 2-(4-chlorophenyl)-4-benzoyl-5-(4-pyridyl)imidazole, For the purposes herein of nomenclature, the compounds of formula I are named by their position corresponding to:

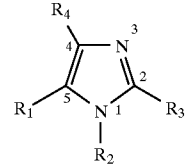

(I)

The invention is described herein in detail using the terms defined below unless otherwise specified.

"Halogen" includes fluorine, chlorine, bromine and iodine.

The term "alkyl" refers to a monovalent alkane (hydrocarbon)-derived radical containing the designated number of carbon atoms. It may be straight or branched. Examples include methyl, ethyl, propyl, butyl, pentyl, hexyl, isopropyl, sec-butyl, isopentyl and t-butyl.

The term "alkenyl" refers to a hydrocarbon radical, straight or branched, containing the designated number of carbon atoms and at least one carbon to carbon double bond. Preferably one carbon to carbon double bond is present, and up to four non- aromatic (non-resonating) carbon-carbon double bonds may be present. Examples of alkenyl groups include ethenyl, propenyl, butenyl and isobutenyl.

The term "alkynyl" refers to a hydrocarbon radical, straight or branched, containing the designated number of carbon atoms and at least one carbon to carbon triple bond. Up to three carbon-carbon triple bonds may be present. Examples of alkynyl groups include ethynyl, propynyl and butynyl.

"Aryl" refers to aromatic rings wherein all ring atoms are carbon, including phenyl and naphthyl.

The term "heteroaryl" (on its own or in any combination, such as "heteroaryloxy") represents a 5–10 membered aromatic ring system in which one or more rings contain one or more heteroatoms selected from the group consisting of N, O and S, such as, but not limited to pyridyl, pyrimidinyl, pyrrolyl, furyl, thienyl, imidazolyl, thiazolyl, thiadiazolyl, tetrazolyl, triazolyl, oxadiazolyl, oxazolyl, imidazolidinyl, pyrazolyl, isoxazolyl, benzothiadiazolyl, indolyl, indolinyl, benzodioxolyl, benzodioxanyl, benzothiophenyl, benzofuranyl, benzimidazolyl, benzoxazinyl, benzisoxazolyl, benzothiazolyl, 2,3-dihydrobenzofuranyl, quinolinyl, isoquinolinyl, benzotriazolyl, benzoxazolyl, 1,2, 3,4-tetrahydroisoquinolinyl, 1,2,3,4-tetrahydroquinolinyl, purinyl, furopyridine and thienopyridine, tetrahydrobenzothiazolyl, 5,6,7,8-tetrahydroquinolinyl, 2,3-cyclopentenopyridyl, 4,5,6,7-tetrahydroindolyl, 5,6,7,8-tetrahydroisoquinolyl, and 5,6,7,8-tetrahydroquinoxalinyl.

"Heterocyclic" (on its own or in any combination, such as "heterocyclylalkyl") represents a saturated or wholly or partially unsaturated 4–10 membered ring system in which one or more rings contain one or more heteroatoms selected from the group consisting of N, O and S. Examples of heterocyclyls are piperidinyl, morpholinyl, pyrrolidinyl, tetrahydrofuranyl, tetrahydroimidazo[4,5-c]pyridine, imidazolinyl, piperazinyl, pyrazolindinyl and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "TNF mediated disease or disease state" refer to disease states in which TNF plays a role, either by production of TNF itself, or by TNF causing another monokine to be released, such as but not limited to IL-1 or IL-6. A disease state in which IL-1, for instance is a major component, and whose production or action, is exacerbated or secreted in response to TNF, would therefore be considered a disease state mediated by TNF.

The term "cytokine" as used herein is meant any secreted polypeptide that affects the functions of cells and is a molecule which modulates interactions between cells in the immune, inflammatory or hematopoietic response. A cytokine includes, but is not limited to, monokines and lymphokines regardless of which cells produce them. Examples of cytokines include, but are not limited to, Interleukin-1 (IL-1), Interleukin-6 (IL-6), Tumor Necrosis Factor-alpha (TNF-α) and Tumor Necrosis Factor-beta (TNF-β).

By the term "cytokine antagonizing, interfering or cytokine suppressive amount" is meant an amount of a compound of formula I which will, cause a decrease in the in vivo presence or level of the cytokine to normal or sub-normal levels, when given to the patient for the prophylaxis or therapeutic treatment of a disease state which is exacerbated by, or caused by, excessive or unregulated cytokine production.

The compounds of the present invention may contain one or more asymmetric carbon atoms and may occur as racemates, racemic mixtures, and as individual diastereomers, with all possible isomers, including optical isomers, being included within the scope of the present invention.

Throughout the instant application, the following abbreviations are used with the following meanings:

aFGF acid fibroblast growth factor
Bu butyl
Bn benzyl
BOC, Boc t-butyloxycarbonyl
BOP Benzotriazol-1-yloxy tris/dimethylarnino)-phosphonium hexafluorophosphate
CBZ, Cbz Benzyloxycarbonyl
DCC Dicyclohexylcarbodiimide
DCM dichloromethane
DIEA diisopropylethylamine
DMF N,N-dimethylformamide
DMAP 4-Dimethylaminopyridine
DSC N,N'-disuccinimidyl carbonate
DTT dithiothreitol
EDC 1-(3-dimethylaminopropyl)-3-ethylcarbodiimide hydrochloride
Et ethyl
EtOAc ethyl acetate
EtOH ethanol
eq. equivalent(s)
FAB-MS Fast atom bombardment-mass spectroscopy
HBGF hemogloblin growth factor
HOAc acetic acid
HPLC High pressure liquid chromatography
HOBT, HOBt Hydroxybenztriazole
H human serum
KHMDS Potassium bis(trimethylsilyl)amide
LAH Lithium aluminum hydride
LHMDS Lithium bis(trimethylsilyl)amide
Me methyl
MHz Megahertz
MPLC Medium pressure liquid chromatography
NMM N-Methylmorpholine
NMR Nuclear Magnetic Resonance
PBS phosphate buffer saline
Ph phenyl
TFA Trifluoroacetic acid
THF Tetrahydrofuran
TLC Thin layer chromatography
TMS Tetramethylsilane The term "pharmaceutically acceptable salts" refers to salts prepared from pharmaceutically acceptable non-toxic acids or bases including inorganic acids/bases and organic acids/bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Salts derived from inorganic acids include hydrochloric, hydrobromic, sulfuric, sulfamic, phosphoric, nitric and the like; and the salts prepared from organic acids include acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

This invention relates to a method of inhibiting the action of glucagon at its receptors thereby reducing the rate of gluconeogenesis and the concentration of glucose in plasma. Thus, compounds of formula I can be used in the prophylaxis or treatment of disease states in mammals mediated by elevated levels of glucagon. Examples of such disease states include diabetes, obesity, hypertension, cachexia, and the like.

This invention also relates to a method of inhibiting the production or activity of cytokines in a mammal in need thereof which comprises administering to said mammal an effective amount of a compound of formula I to inhibit cytokine production or activity such that it is regulated down to normal levels, or in some cases to subnormal levels, so as to ameliorate or prevent the disease state.

The compounds of formula I can be used in the manufacture of a medicament for the prophylactic or therapeutic treatment of disease states in mammals, which are exacerbated or caused by excessive or unregulated cytokine production, more specifically IL-1, IL-6, IL-8 or TNF production, by such mammal's cells, such as but not limited to monocytes and/or macrophages.

Compounds of formula I inhibit cytokines, such as IL-1, IL-6, IL-8 and TNF and are therefore useful for treating inflammatory diseases such as rheumatoid arthritis, rheumatoid spondylitis, osteoarthritis, gouty arthritis and other arthritic conditions.

The compounds of formula I may be used to treat other disease states mediated by excessive or unregulated cytokine production or activity. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (AIDs related complex), keloid formation, scar tissue formation, Crohn's disease, ulcerative colitis, pyresis, AIDS and other viral infections, such as cytomegalovirus (CMV), influenza virus, and the herpes family of viruses such as Herpes Zoster or Simplex I and II.

The compounds of formula I may also be used topically in the treatment of inflammation such as for the treatment of rheumatoid arthritis, rheumatoid spondylitis, osteoarthritis, gouty arthritis and other arthritic conditions; inflamed joints, eczema, psoriasis and other inflammatory skin conditions such as sunburn; inflammatory eye conditions including conjunctivitis; pyresis, pain and other conditions associated with inflammation.

Interleukin-1 (IL-1) has been demonstrated to mediate a variety of biological activities thought to be important in immunoregulation and other physiological conditions. [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout traumatic arthritis, rubella arthritis, and acute synovitis. Recent evidence also links IL-1 activity to diabetes and pancreatic β cells.

The compounds of formula I are also useful in treating diseases characterized by excessive IL-8 activity. There are many disease states in which excessive or unregulated IL-8 production is implicated in exacerbating and/or causing the disease. These diseases include psoriasis, inflammatory bowel disease, asthma, cardiac and renal reperfusion injury, adult respiratory distress syndrome, thrombosis and glomerulonephritis. The invention includes a method of treating psoriasis, inflammatory bowel disease, asthma, cardiac and renal reperfusion injury, adult respiratory distress syndrome, thrombosis and glomerulonephritis, in a mammal in need of such treatment which comprises administering to said mammal a compound of formula I in an amount which is effective for treating said disease or condition.

The compounds of formula I are normally formulated in accordance with standard pharmaceutical practice as a pharmaceutical composition. This invention, therefore, also relates to a pharmaceutical composition comprising a compound of formula I and a pharmaceutically acceptable carrier or diluent. The pharmaceutical carrier employed may be, for example, solid or liquid. Solid carriers include lactose, terra alba, sucrose, talc, gelatin, agar, pectin, acacia, magnesium stearate, stearic acid and the like. Liquid carriers include syrup, peanut oil, olive oil, water and the like. Similarly, the carrier may include time delay material, such as glyceryl monostearate or glyceryl distearate, alone or with a wax.

The compounds of formula I are administered in conventional dosage forms prepared by combining a compound of formula I with standard pharmaceutical carriers according to conventional procedures. The compounds of formula I may also be administered in conventional dosages in combination with a known, second therapeutically active compound. These procedures may involve mixing, granulating and compressing or dissolving the ingredients as appropriate to the desired preparation.

The active compounds of the present invention may be orally administered as a pharmaceutical composition, for example, with an inert diluent, or with an assimilable edible carrier, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally, for example intravenously, intramuscularly, intradermally or subcutaneously. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of formula I may also be administered topically in the form of a liquid, solid or semi-solid. Liquids include solutions, suspensions and emulsions. Solids include powders, poultices and the like. Semi-solids include creams, ointments, gels and the like.

Drops according to the present invention may comprise sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous liquid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as propylene glycol or macrogels. The formulation may incorporate any suitable surface active agent such as an anionic, cationic or non-ionic surfactant such as sorbitan esters or polyoxyethylene derivatives thereof. Suspending agents such as natural gums, cellulose derivatives or inorganic materials such as silicas, and other ingredients such as lanolin may also be included.

Compounds of the present invention may also be administered intranasally as, for example, liquid drops or spray; by intranasal or oral inhalation; rectally; trasdermally; or vaginally.

The amount of a compound of formula I, for the methods of use disclosed herein, vary with the compound chosen, the mode of administration, the nature and severity of the condition being treated, and other factors left to the discretion of the physician. A representative dosing regimen for treating diabetes mellitus and/or hyperglycemia may involve administering a compound of formula I at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

Compounds similar to Formula I have been described previously as cytokine inhibitors (WO93/14081; WO95/03297), antiinflammatory agents (WO96/03387), and protein kinase inhibitors (WO96/18626). None of these publications describe or claim treatment of diabetes by antagonism of the glucagon receptor.

Compounds of the present invention may be prepared by several general synthetic methods as described in, for example, M. R. Grimmett, *Comprehensive Heterocyclic Chemistry, The Structure, Reactions, Synthesis and Uses of Heterocyclic Compounds*, A. R. Katritzky and C. W. Rees, eds., Vol. 5, Pergamon Press, Oxford, 1984, pp. 457–498. The compounds of the present invention can be prepared by procedures illustrated in the accompanying schemes. The three general methods for preparation of the imidazole nucleus are outlined in schemes 1, 2, and 3.

In the first method (Scheme 1), a suitably protected picolyl alcohol (I) is deprotonated with a strong base such as lithium diisopropyl amide or n-butyl lithium and the resulting anion is reacted with an appropriate N,O-dimethylhydroxamide (2) to give a protected alpha hydroxy ketone (3). The protected alpha hydroxy ketone is then condensed with a suitably functionalized aldehyde (4) in the presence of copper (II) acetate and ammonium acetate in acetic acid to form the desired compound.

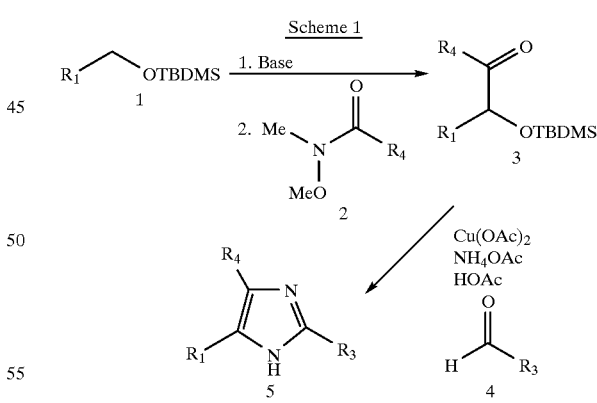

In the second method (Scheme 2), picoline (6) is deprotonated with a strong base such as lithium diisopropyl amide or n-butyl lithium and the resulting anion is reacted with N,O-dimethylhydroxamide (2) to give a pyridylarylmethyl ketone (7). The dione (8) obtained by selenium dioxide oxidation of the pyridylarylmethyl ketone is then condensed with a suitably functionalized aldehyde (4) in the presence of ammonium acetate in acetic acid to form the desired imidazole (5).

Scheme 2

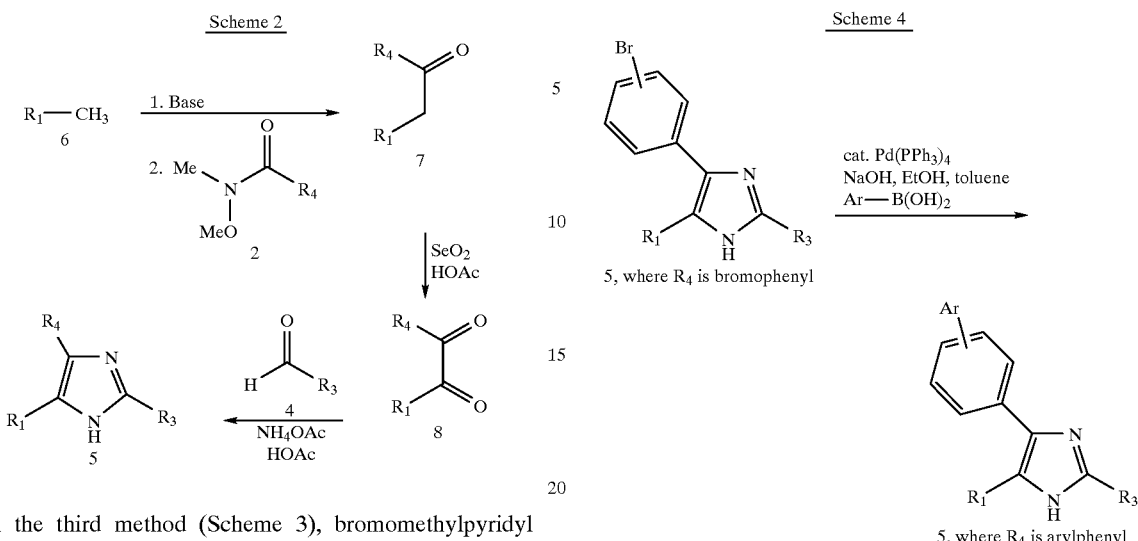

Scheme 4

In the third method (Scheme 3), bromomethylpyridyl ketone (9) is reacted with a suitably substituted benzamidine (10) to afford the disubstituted imidazole (11) which is then protected. The protected imnidazole (12) is deprotonated with a strong base such as n-butyl lithium, s-butyl lithium, or lithium diisopropyl amide followed by reaction with the appropriate alkylating or acylating agent (13, L may be for example halogen, alkylsulfonate, arylsulfonate, activated ester) yields the protected target compound. Removal of the N-protection on the imidazole affords the target compound (14).

In the various synthetic methods described above, protection and deprotection of functional groups such as hydroxyl and amino groups may be required. The selection of the appropriate protecting groups, and methods for introducing and removing the protecting groups are within the knowledge of one skilled in the art, and are also described in standard reference books such as Greene and Wuts, Scheme 3

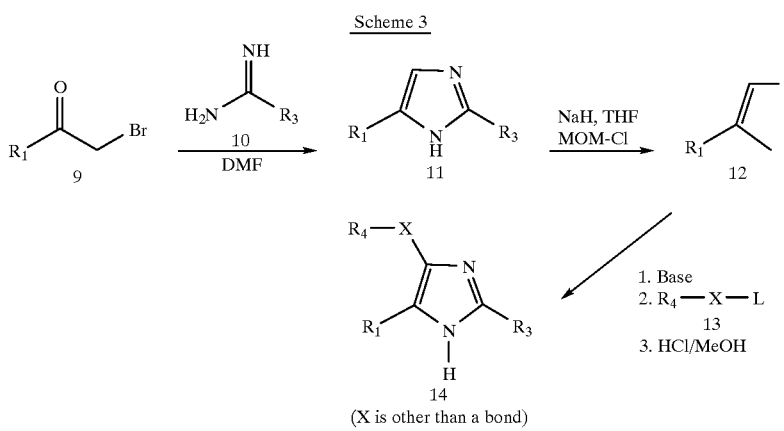

In some instances where the biaryl moiety had not been established, palladium(0)-catalyzed biaryl coupling reactions with suitable boronic acids may be carried out after the imidazole nucleus has been formed to provide the final biaryl compounds; thus 5 where $R_4$ is bromophenyl may be converted to the corresponding biaryl compound 5 where $R_4$ is arylphenyl using a catalytic amount of palladium tetrakis (triphenylphosphine) and the appropriate arylboronic acid as shown in Scheme 4.

*Protective Groups in Organic Synthesis,* 2d Ed., John Wiley & Sons, Inc., 1991.

The following examples are provided to more fully illustrate the invention, and are not to be construed as limiting the scope of the invention in any manner.

EXAMPLE 1

2-(4-Chlorophenyl)-4-(4'-ethyl-4-biphenyl)-5-(4-pyridyl)imidazole

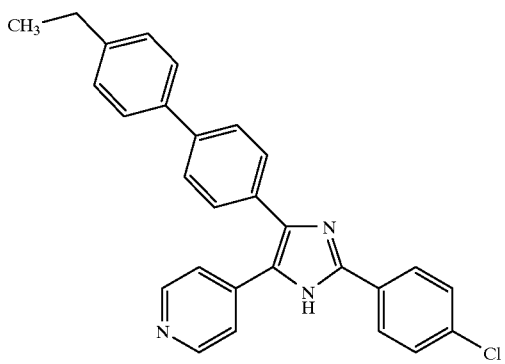

Step A: 4-t-Butydimethylsilyloxymethylpyridine

To a solution of 4-pyridylcarbinol (50.3 g, 0.46 mol) in methylene chloride (250 mL) under a dry nitrogen atmosphere was added triethylamine (97 mL, 0.69 mol). To this mixture was added dropwise tert-butyl-dimethylsilyl chloride (83.7 g, 0.555 mol) with cooling (T 34° C.). The reaction mixture was stirred overnight at room temperature. The slurry was then filtered and the solvent removed by rotoevaporation. The residue was suspended in toluene and filtered and the solvent removed by rotoevaporation. The residue was suspended in diethyl ether and filtered and the solvent removed by rotoevaporation. The same process was repeated with hexanes to yield 4-t-butydimethylsilyloxymethylpyridine as a brown oil.

Step B: 4'-Ethyl-4-biphenyl 4-pyridyl-t-butyldimethylsilyloxymethyl ketone

To a cooled solution of diisopropylamine (188 mg, 1.86 mmol) in THF (0.4 mL) at −20° C. under a dry nitrogen atmosphere was added a solution of n-butyllithium in hexanes (0.86 mL of a 2.5 M solution, 2.14 mmol). After stirring at −20° C. for 1 h, a solution of 4-t-butyldimethylsilyloxymethylpyridine from Step A (394 mg, 1.77 mmol) in THF (0.4 mL) was added dropwise. After stirring at −20° C. for 1 h, a solution of 4'-ethyl-N-methoxy-N-methyl-4-biphenylcarboxamide (500 mg, 1.86 mmol, prepared from 4'-ethyl-4-biphenyl carboxylic acid according to the procedure described in Example 1, Step A) in THF (0.5 mL) was added. After stirring the reaction mixture at −20 to −10° C. for 5 h, the reaction was quenched by the addition of a saturated aqueous solution of ammonium chloride. The mixture was extracted with ethyl acetate (3 times) and the combined organic extracts were successively washed with water (2 times) and saturated salt solution. The solution was dried over anhydrous sodium sulfate and filtered. The solvent was removed by rotoevaporation and the residue purified by flash column chromatography on silica gel eluted with 0–5% ethyl acetate in hexanes to afford the title compound as a yellow oil (290 mg, 36% yield).

Step C: 2-(4-Chlorophenyl)-4-(4'-ethyl-4-biphenyl)-5-(4-pyridyl)imidazole

A solution of 4'-ethyl-4-biphenyl 4-pyridyl-t-butyldimethylsilyloxymethyl ketone from Step C (145 mg, 0.34 mmol), copper (II) acetate (122 mg, 0.67 mmol), ammonium acetate (259 mg, 3.36 mmol) and 3-chlorobenzaldehyde (59 mg, 0.42 mmol) in acetic acid (3 mL) was heated to 110° C. for 5 h. After cooling to 0° C., ice (4 g), ethyl acetate (4 mL) and an aqueous concentrated ammonium hydroxide solution (4 mL) was added. After stirring for 30 min, the layers were separated. The aqueous layer was extracted with ethyl acetate (2 times) and the combined organic phases were successively washed with water (2 times) and a saturated salt solution. The solution was dried over anhydrous sodium suflate, filtered and the solvent removed by rotoevaporation. The residue was purified by flash column chromatography on silica gel eluted with 0–3% methanol in methylene chloride to afford the title compound as a pale yellow solid (78 mg, 53% yield), mass spectrum (CI) m/e=436 (M+1)$^+$.

The following compounds were prepared by methods analogous to those described in Example 1 except the appropriately substituted N-methoxy-N-methylbenzamide and substituted benzaldehyde was used in place of 4'-ethyl-N-methoxy-N-4-biphenylcarboxamide and 4-chlorobenzaldehyde, respectively.

4-(4-biphenyl)-2-(4-chlorophenyl)-5-(4-pyridyl)imidazole, mass spectrum (CI) m/e=408 (M+1)$^+$.

4-(4-biphenyl)-2-(3-chlorophenyl)-5-(4-pyridyl)imidazole, mass spectrum (CI) m/e=408 (M+1)$^+$.

2-(3-chlorophenyl)-4-(4'-ethyl-4-biphenyl)-5-(4-pyridyl)imidazole, mass spectrum (CI) m/e=436 (M+1)$^+$.

EXAMPLE 2

1-(t-butyloxycarbonyl)-5-(4-fluorophenyl)-2-(4-phenoxyphenyl)-4-(4-pyridyl)imidazole

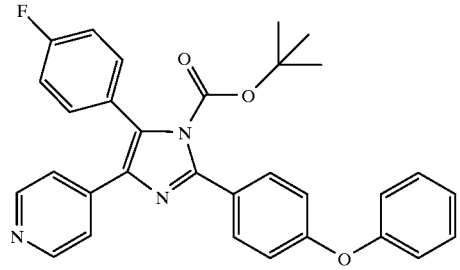

To a solution of 2-(4-phenoxyphenyl)-4-(4-fluorophenyl)-5-(4-pyridyl)imidazole (prepared by the method described in Example 2; 150 mg, 0.37 mmol) in DMF (1 mL) was added solid sodium hydride (8.9 mg of a 60% oil dispersion, 0.37 mmol). The reaction was stirred for 1 h at room temperature and then cooled to −20° C. Di-t-butyl carbonate (85 μL, 0.37 mmol) was added and the reaction was placed in a refrigerator for 4 days. The reaction was quenched by the addition of water and the mixture was extracted with ethyl acetate (3 times). The combined extracts were successively washed with water (2 times) and saturated salt solution and dried over anhydrous sodium sulfate. The solution was filtered and the solvent removed by rotoevaporation. The residue was purified by flash column chromatography on silica gel eluted with 0–1.5% methanol in methylene chloride to yield the title compound, mass spectrum (CI) m/e=508 (M+1)$^+$.

The following compound was prepared by methods analogous to those described in Example 2 except ethyl chloroformate was used in place of di-t-butyl carbonate.

1-(ethoxycarbonyl)-5-(4-fluorophenyl)-2-(4-phenoxyphenyl)-4-(4-pyridyl)imidazole, mass spectrum (CI) m/e=480 (M+l)$^+$.

EXAMPLE 3

4-Benzoyl-2-(4-chlorophenyl)-5-(4-pyridyl) imidazole

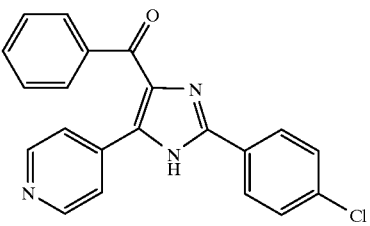

Step A: 2-(4-chlorophenyl)-4-(4-pyridyl)imidazole

To a cooled solution of 4-chlorobenzamidine (3.4 g, 22 mmol) in DMF (12 mL) at 0° C. was added batchwise bromomethyl 4-pyridyl ketone hydrobromide (1.47 g, 5.5 mmol) over a 15 min period. The reaction was stirred for 30 min at room temperature. The reaction was quenched by the addition of saturated ammonium chloride solution and the mixture was extracted with ethyl acetate (2 times). The combined extracts were successively washed with water (2 times) and saturated salt solution and dried over anhydrous sodium sulfate. The solution was filtered and the solvent removed by rotoevaporation. The residue was purified by flash column chromatography on silica gel eluted with 0–1.5% methanol in methylene chloride to yield the title compound, mass spectrum (CI) m/e=256 (M+1)$^+$.

Step B: 2-(4-chlorophenyl)-1-methoxymethyl-5-(4-pyridyl) imidazole

To a solution of 2-(4-chlorophenyl)-4-(4-pyridyl) imidazole from Step A (200 mg, 0.78 mmol) in THF (8 mL) at room temperature was added sodium hydride (63 mg of a 60% oil dispersion, 1.57 mmol). After cooling to 0° C., methoxymethyl chloride (74 µL, 0.97 mmol) was slowly added. The reaction was stirred at 0 oC for 1 h, then at room temperature for 1 h. The reaction was quenched by the addition of 5% sodium bicarbonate solution and the mixture was extracted with ethyl acetate (2 times). The combined extracts were successively washed with 5% sodium bicarbonate solution, water and saturated salt solution and dried over anhydrous sodium sulfate. The solution was filtered and the solvent removed by rotoevaporation. The residue was purified by flash column chromatography on silica gel eluted with 0–3% methanol in methylene chloride to yield the title compound as a pale yellow solid (172 mg, 72% yield), mass spectrum (CI) m/e=300 (M+1)$^+$.

Step C: 4-Benzoyl-2-(4-chlorophenyl)-1-methoxymethyl-5-(4-pyridyl)imidazole

To a cooled solution of 2-(4-chlorophenyl)-1-methoxymethyl-5-(4-pyridyl)imidazole from Step B (40 mg, 0.13 mmol) in THF (0.5 mL) at –30° C. was added dropwise a solution of n-butyllithium in hexanes (93 µL of a 2.5 M solution, 0.23 mmol). The reaction was stirred at –30 to –10° C. for 90 min. After cooling to –30° C., benzoyl chloride (47 µL, 0.40 mmol) was added. The reaction was stirred overnight at room temperature. The reaction was quenched by the addition of saturated ammonium chloride solution and the mixture was extracted with ethyl acetate (2 times). The combined extracts were successively washed with water and saturated salt solution and dried over anhydrous sodium sulfate. The solution was filtered and the solvent removed by rotoevaporation. The residue was purified by flash column chromatography on silica gel eluted with 0–4% methanol in methylene chloride to yield the title compound as a red-brown glass (14 mg, 26% yield), mass spectrum (CI) m/e=404 (M+1)$^+$.

Step D: 4-Benzoyl-2-(4-chlorophenyl)-5-(4-pyridyl) imidazole

A solution of 4-benzoyl-2-(4-chlorophenyl)-1-methoxymethyl-5-(4-pyridyl)imidazole (10 mg, 0.025 mmol) in methanol (0.8 mL) containing 6 N hydrochloric acid (21 µL) at 40° C. was stirred overnight. The reaction was quenched by the addition of 5% sodium bicarbonate solution and the mixture was extracted with ethyl acetate (2 times). The combined extracts were successively washed with water and saturated salt solution and dried over anhydrous sodium sulfate. The solution was filtered and the solvent removed by rotoevaporation. The residue was purified by flash column chromatography on silica gel eluted with 0–3% methanol in methylene chloride to yield the title compound as a orange glass (4 mg, 40% yield), mass spectrum (CI) m/e=360 (M+1)$^+$.

The following compound was prepared by methods analogous to those described in Example 3 except 2-biphenylmethyl bromide was used in place of benzoyl chloride.

2-(4-chlorophenyl)-4-(2-biphenyl)methyl-5-(4-pyridyl) imidazole, mass spectrum (CI) m/e=422 (M+1)$^+$.

EXAMPLE 4

2-(4-Chlorophenyl)-4-(4'-methoxybiphenyl-4-yl)-5-(4-pyridyl)imidazole

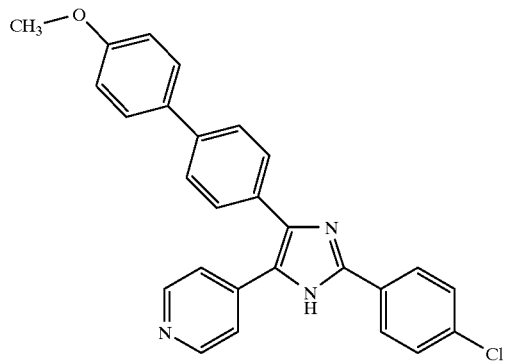

Step A: 1-(4-Bromophenyl)-2-(4-pyridyl)-ethanone

To a stirred solution of diisopropyl amine (358 mg, 3.54 mmol) in THF (3 mL) cooled to –45° C. was added dropwise n-butyl lithium (1.6 mL, 4.0 mmol, of a 2.5M solution in hexanes). The reaction was stirred between –45 and –10° C. for 0.75 h. After being cooled to –78° C., 4-picoline (300 mg, 3.22 mmol) in THF (1 mL) was added dropwise. The reaction was stirred at –78 to –30° C. for 1.5 h. At –78° C., 825 mg (3.38 mmol) of 3-bromo-N-methoxy-N-methylbenzamide (prepared from the corresponding acyl chloride according to Example 1, Step A) dissolved in 2 mL of THF was added dropwise. After standing at –20° C. for 16 h, the reaction mixture was quenched by addition of half saturated aqueous ammonium chloride at –20° C. Phases were separated and the aqueous layer was extracted with ethyl acetate (3×7 mL). The organic layers were combined, washed with water, brine, dried with sodium sulfate, and evaporated under reduced pressure. The residue was flash chromatographed over silica gel, (gradient elution using 10–25% EtOAc in hexane). A homogeneous fraction of 437 mg of desired product was collected as a yellow oil along with 350 mg of recovered starting amide; homogeneous in 1:1 EtOAc/hexane; mass spectrum (CI) m/e 276,278 (M+1)$^+$.

Step B: 1-(4-Bromophenyl)-2-(4-pyridyl)-ethan-1,2-dione

A mixture of 200 mg (0.725 mmol) of 1-(4-bromophenyl)-2-(4-pyridyl)-ethanone (from Step A) and 81 mg (0.725 mmol) of selenium(IV) oxide, and 5.5 mL of glacial acetic acid was heated to 135° C. for 2 h. After being cooled to room temperature, the reaction mixture was partitioned between saturated aqueous potassium carbonate and ethyl acetate. The aqueous layer was extracted twice more more with ethyl acetate. The organic layers were combined and washed with water and brine and dried over anhydrous sodium sulfate. Volatiles were removed under reduced pressure and the residue was flash chromatographed over silica gel (gradient elution 2–4% MeOH in DCM) to yield 100 mg of the titled compound, homogeous by TLC; mass spectrum (CI) m/e 290, 292 $(M+1)^+$.

Step C: 4-(4-Bromophenyl)-2-(4-chlorophenyl)-5-(4-pyridyl)imidazole

A mixture of 100 mg (0.345 mmol) of 1-(4-bromophenyl)-2-(4-pyridyl)-ethan-1,2-dione (from Step B), 266 mg (3.45 mmol) of ammonium acetate, and 61 mg (0.0.431 mmol) of 4-chlorobenzaldehyde in 2 mL of acetic acid was heated at 90° C. for 3 h. The green reaction mixture was treated with excess 2:1 $NH_4$ OH/sat. $NH_4Cl$ and extracted with ethyl acetate and chloroform 3 times. The organic layers were combined and washed with water, brine, and dried over sodium sulfate. After removal of solvents, the residue was flash chloromatographed over silica gel (gradient elution, 1–4% MeOH in DCM) to give 75 mg of the titled compound, homogeneous by TLC (9:1 DCM/MeOH); mass spectrum (CI) m/e 411, 413 $(M+1)^+$.

Step D: 2-(4-Chlorophenyl)-4-(4'-methoxybiphenyl-4-yl)-5-(4-pyridyl)imidazole

To a solution of 60 mg (0.146 mmol) of 4-(4-bromophenyl)-2-(4-chlorophenyl)-5-(4-pyridyl)imidazole (from Step C) in 1 mL of ethanol and 1.5 mL of toluene was added 56 mg (0.365 mmol) of 4-methoxybenzeneboronic acid, followed by 0.73 mmol (584 $\mu$L of a 1.25 N solution) of aqueous NaOH, and 17 mg (0.146 mmol) of tetrakis (triphenylphosphine)palladium(0). The resulting reaction mixture was stirred at 90° C. overnight. After being cooled to room temperature, the reaction was quenched by addition of water and extracted with ethyl acetate twice. The organic layers were combined, washed with water and brine, and dried over sodium sulfate. After filtration and removal of volatiles, the crude product was flash chromatographed over silica gel (gradient elution using 20–50% EtOAc in hexane). This material appeared to be homogeneous by TLC but contained some uncoupled material as shown by HPLC trace. Therefore, it was further purified via a chromatotron, eluting slowly using a 5:95:0.5 mixture of methanol/DCM/HOAc to provide 16 mg of the desired product as a pale yellow solid, homogeneous by TLC, mass spectrum (CI) m/e 438 $(M+1)^+$.

The following compounds were prepared by methods analogous to those described in Example 1 except the appropriately substituted N-methoxy-N-methylbenzamide and substituted benzaldehyde was used in place of 4'-ethyl-N-methoxy-N-4-biphenylcarboxamide and 4-chlorobenzaldehyde, respectively.

2-(4-chlorophenyl)-4-(4-(1-naphthyl)phenyl)-5-(4-pyridyl)imidazole, mass spectrum (CI) m/e=458 $(M+1)^+$.

2-(4-chlorophenyl)-4-(3'-methoxy-4-biphenyl)-5-($^4$-pyridyl)imidazole, mass spectrum (CI) m/e=438 $(M+1)^+$.

2-(4-chlorophenyl)-4-(2'-methoxy-4-biphenyl)-5-($^4$-pyridyl)imidazole, mass spectrum (CI) m/e=438 $(M+1)^+$.

2-(4-chlorophenyl)-5-(4-pyridyl)-4-($^4$-($^2$-thienyl)phenyl) imidazole, mass-spectrum (CI) m/e=414 $(M+1)^+$.

2-(4-chlorophenyl)-4-(4'-methoxy-3-biphenyl)-5-($^4$-pyridyl)imidazole, mass spectrum (CI) m/e=438 $(M+1)^+$.

2-(4-chlorophenyl)-4-(3'-methoxy-3-biphenyl)-5 -(4-pyridyl)imidazole, mass spectrum (CI) m/e=438 $(M+1)^+$.

2-(4-chlorophenyl)-4-(4'-(4-methoxybenzylthio)-4-biphenyl)-5-(4-pyridyl)imidazole, mass spectrum (CI) m/e=560 $(M+1)^+$.

4-(3-biphenyl)-2-(4-chlorophenyl)-5-(4-pyridyl) imidazole, mass spectrum (CI) m/e=408 $(M+1)^+$.

2-(4-chlorophenyl)-4-(2'-methoxy-3-biphenyl)-5-($^4$-pyridyl)imidazole, mass spectrum (CI) m/e=438 $(M+1)^+$.

2-(4-chlorophenyl)-4-(3-(1-naphthyl)phenyl)-5-(4-pyridyl)imidazole, mass spectrum (CI) m/e=458 $(M+1)^+$.

2-(4-chlorophenyl)-4-(2',4'-dichloro-3-biphenyl)-5-(4-pyridyl)imidazole, mass spectrum (CI) m/e=476 $(M+1)^+$.

2-(4-chlorophenyl)-4-(3-(2-naphthyl)phenyl)-5-(4-pyridyl)imidazole, mass spectrum (CI) m/e=458 $(M+1)^+$.

2-(4-chlorophenyl)-4-(4'-chloro-3-biphenyl)-5-(4-pyridyl)imidazole, mass spectrum (CI) m/e=442 $(M+1)^+$.

2-(4-chlorophenyl)-4-(3'-chloro-3-biphenyl)-5-(4-pyridyl)imidazole, mass spectrum (CI) m/e=442 $(M+1)^+$.

2-(4-chlorophenyl)-4-(3',5 '-dichloro-3-biphenyl)-5-(4-pyridyl)imidazole, mass spectrum (CI) m/e=476, 478 $(M+1)^+$.

2-(4-chlorophenyl)-4-(4'-(4-methoxybenzylthio)-3-biphenyl)-5-(4-pyridyl)imidazole, mass spectrum (CI) m/e=560 $(M+1)^+$.

2-(4-chlorophenyl)-4-(3-(2-thienyl)phenyl)-5-(4-pyridyl) imidazole, mass spectrum (CI) m/e=414 $(M+1)^+$.

2-(4-chlorophenyl)-4-(3-(3-thienyl)phenyl)-5-(4-pyridyl) imidazole, mass spectrum (CI) m/e=414 $(M+1)^+$.

2-(4-chlorophenyl)-4-(2',4-dimethoxy-3-biphenyl)-5-(4-pyridyl)imidazole, mass spectrum (CI) m/e=468 $(M+1)^+$.

BIOLOGICAL ASSAYS

The ability of compounds of the present invention to inhibit the binding of glucagon and the synthesis or the activity of cytokines can be determined by the following in vitro assays.

$^{125}$I-Glucagon Binding Screen with CHO/hGLUR Cells

The reagents are prepared as follows:

1M o-Phenanthroline (Aldrich #32,005-6, MW 198.23) (prepare fresh): 198.2 mg/ml ethanol 0.5M DTT (Sigma #D-9779, MW 154.2) (prepare fresh).

Protease Inhibitor Mix (10000X): 5 mg leupeptin +10 mg benzamidine +40 mg bacitracin +5 mg soybean trypsin inhibitor per ml DMSO. Store aliquots at −20° C.

250 $\mu$M Human Glucagon (Peninsula #7165,MW 3480.62): Solubilize 0.5 mg vial in 575 $\mu$l 0.1 N acetic acid. Store in aliquots at −20° C. Thus, 1 $\mu$l yields 1 $\mu$M final concentration in assay for non-specific binding.

Assay Buffer: 20 mM Tris, pH 7.8; 1 mM DTT; 3 mM o-phenanthroline. Assay Buffer w/0.% BSA (for dilution of label only, therefore 0.01% final in assay): 10 $\mu$l 10% BSA (heat-inactivated) +990 $\mu$l assay buffer $^{125}$I-Glucagon (NEN #NEX-207, receptor-grade, 2200 Ci/mmol): Dilute to 50,000 cpm/25 µl in assay buffer w/BSA. Thus, ~50 pM final concentration in assay.

Harvesting of CHO/hGLUR Cells for Assay:

1. Remove media from confluent flask then rinse once each with PBS (Ca, Mg-free) and Enzyme-free Dissociation Fluid (Specialty Media, Inc.).
2. Add 10 ml Enzyme-free Dissoc. Fluid and hold for ~4 min. at 37° C.
3. Gently tap cells free, triturate, take aliquot for counting and centrifuge remainder for 5 min. at 1000 rpm.
4. Resuspend pellet in assay buffer (no BSA) at 75000 cells per 100 µl.

Alternatively, membrane preparations from CHO/hGLUR cells can be used in place of whole cells at the same assay volume. Final protein concentration of membrane preparation is determined on a per batch basis.

The determination of inhibition of glucagon binding is carried out by measuring the reduction of $I^{125}$-glucagon binding in the presence of compounds of Formula I. The assay is carried out in a 96-well box. The following reagents are combined:

|  | Assay CHO/hGLUR Buffer Cells | Compound/ Vehicle | 250 uM Glucagon | $^{125}$I- Glucagon |
|---|---|---|---|---|
| Total 100 µL Binding | 120 µL | —/5 µL | — | 25 µL |
| +compound 100 µL | 120 µL | 5 µL/— | — | 25 µL |
| NSB 100 µL | 120 µL | —/5 µL | 1 µL | 25 µL |

NSB: non specific binding

The box is incubated for 60 min. at 22° C. on a shaker at 275 rpm. The wells are filtered over pre-soaked (0.5% polyethylimine(PEI)) GF/C filtermat using an Innotech Harvester or Tomtec Harvester with four washes of ice-cold 20 mM Tris, pH 7.8 buffer. Count filters in Gamma-scintillation counter.

Lipopolysaccharide mediated production of cytokines

Human peripheral blood mononuclear cells (PBMC) are isolated from fresh human blood according to the procedure of Chin and Kostura, J. *Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2 \times 10^6$ cell/mL in RPMI containing 10% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL. An aliquot (0.1 mL) of the cells is quickly dispensed into each well of a 96 well plate containing 0.1 mL of the test compound, at the appropriate dilution, and are incubated for 24 h. at 37° C. in 5% $CO_2$. At the end of the culture period, cell culture supernatants are assayed for IL-1β, TNF-α, IL-6 and $PGE_2$ production using specific ELISA.

IL-1 mediated cytokine production

Human peripheral blood mononuclear cells are isolated from fresh human blood according to the procedure of Chin and Kostura, J. *Immunol.* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2 \times 10^6$ cell/mL in RPMI containing 10% fresh autologous human serum, penicillin streptomycin (10 U/mL) and 0.05% DMSO. Endotoxin free recombinant human IL-1β is then added to a final concentration of 50 pMolar. An aliquot (0.1 mL) of the cells is quickly dispensed into each well of a 96 well plate containing 0.1 mL of the compound at the appropriate dilution. and are incubated for 24 h at 37° C. in 5% $CO_2$. At the end of the culture period, cell culture supernatants are assayed for TNF-α, IL-6 and $PGE_2$ synthesis using specific ELISA.

Determination of IL-1β, TNF-α, IL-6 and prostanoid production from LPS or IL-1 stimulated PBMC's

IL-1βELISA

Human IL-1β can be detected in cell-culture supernatants or whole blood with the following specific trapping ELISA. Ninety-six well plastic plates (Immulon 4; Dynatech) are coated for 12 h at 4° C. with 1 mg/mL protein-A affinity chromatography purified mouse anti-human IL-1β monoclonal antibody (purchased as an ascites preparation from LAO Enterprise, Gaithersburg Md.) diluted in Dulbecco's phosphate-buffered saline (—$MgCl_2$, —$CaCl_2$). The plates are washed with PBS-Tween (Kirkegaard and Perry) then blocked with 1% BSA diluent and blocking solution (Kirkegaard and Perry) for 60 minutes at room temperature followed by washing with PBS Tween. IL-1β standards are prepared from purified recombinant IL-1β produced from *E. coli*. The highest concentration begins at 10 ng/mL followed by 11 two-fold serial dilution's. For detection of IL-1β from cell culture supernatants or blood plasma, 10–25 mL of supernatant is added to each test well with 75–90 mL of PBS Tween. Samples are incubated at room temperature for 2 h then washed 6 times with PBS Tween on an automated plate washer (Dennly). Rabbit anti-human IL-1β polyclonal antisera diluted 1:500 in PBS-Tween is added to the plate and incubated for 1 h at room temperature followed by six washes with PBS-Tween. Detection of bound rabbit anti-IL-1β IgG is accomplished with Fab' fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color intensity on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-α ELISA

Immulon 4 (Dynatech) 96-well plastic plates are coated with a 0.5 mg/mL solution of mouse anti-human TNF-60 monoclonal antibody. The secondary antibody is a 1:2500 dilution of a rabbit anti-human TNF-α polyclonal serum purchased from Genzyme. All other operations are identical to those described above for IL-1β. The standards are prepared in PBS-Tween +10% FBS or H. Eleven 2 fold dilution's are made beginning at 20 ng/mL TNF-α.

IL-6 ELISA

Levels of secreted human IL-6 are also determined by specific trapping ELISA as described previously in thin and Kostura, J. *Immunol.* 151, 5574–5585 (1993). (Dynatech) ELISA plates are coated with mouse anti-human IL-6 monoclonal antibody diluted to 0.5 mg/ml in PBS. The secondary antibody, a rabbit anti-human IL-6 polyclonal antiserum, is diluted 1:5000 with PBS-Tween. All other operations are identical to those described above for IL-1β. The standards are prepared in PBS-Tween +10% FBS or H. Eleven 2 fold dilution's are made beginning at 50 ng/mL IL-6.

$PGE_2$ production

Prostaglandin E2 is detected in cell culture supernatants from LPS or IL-1 stimulated PBMC's using a commercially available enzyme immunoassay. The assay purchased from the Cayman Chemical (Catalogue number 514010) and is run exactly according to the manufacturers instructions.

Interleukin8 (IL-8)

The present compounds can also be assayed for IL-8 inhibitory activity as discussed below. Primary human umbilical cord endothelial cells (HUVEC) (Cell Systems, Kirland, Wash.) are maintained in culture medium supplemented with 15% fetal bovine serum and 1% CS-HBGF consisting of (αFGF and heparin. The cells are then diluted 20-fold before being plated (250 μl) into gelatin coated 96-well plates. Prior to use, culture medium is replaced with fresh medium (200μl). Buffer or test compound (25 μl, at appropriate concentrations) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/ml) of multiple samples based on the standard curve. $IC_{50}$ values where appropriate are generated by non-linear regression analysis.

What is claimed is:

1. A compound having the formula (I)

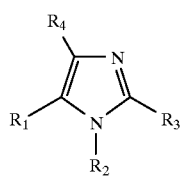

(I)

wherein $R_1$ is 4-pyridyl, which is unsubstituted or substituted with one or two substituents each of which is independently selected from the group consisting of
  (1) halogen,
  (2) —CN,
  (3) $C_{1-10}$ alkyl, wherein said alkyl is optionally substituted with from 1 to 5 halogen atoms,
  (4) —O—$C_{1-10}$ alkyl,
  (5) —S—$C_{1-10}$ alkyl,
  (6) —$NR_8R_9$, and
  (7) —$NO_2$;

$R_2$ is hydrogen, —C(Z)O$C_{1-4}$alkyl, —C(Z)$C_{1-4}$alkyl, or —$S(O)_2C_{1-4}$alkyl;

$R_3$ is phenyl, 1-naphthyl, 2-naphthyl or pyridyl each of which is unsubstituted or substituted with one, two or three substituents each of which is independently selected from the group consisting of
  (1) $C_{1-10}$ alkyl,
  (2) $R_5$, and
  (3) $C_{1-10}$ alkyl substituted with up to 5 groups independently selected from $R_5$;

$R_4$ is —X—Ar wherein

X is a bond and Ar is substituted phenyl, substituted 1-naphthyl, or substituted 2-naphthyl, wherein said substituent is one or two groups each of which is independently selected from the group consisting of
  (1) phenyl, optionally substituted with up to 5 groups independently selected from $C_{1-10}$ alkyl, $R_5$, and $C_{1-10}$ alkyl substituted with up to 5 groups independently selected from $R_5$,
  (2) 1-naphthyl, optionally substituted with up to 5 groups independently selected from $C_{1-10}$ alkyl, $R_5$, and $C_{1-10}$ alkyl substituted with up to 5 groups independently selected from $R_5$,
  (3) 2-naphthyl, optionally substituted with up to 5 groups independently selected from $C_{1-10}$ alkyl, $R_5$, and $C_{1-10}$ alkyl substituted with up to 5 groups independently selected from $R_5$,
  (4) pyridyl, optionally substituted with up to 5 groups independently selected from $C_{1-10}$ alkyl, $R_5$, and $C_{1-10}$ alkyl substituted with up to 5 groups independently selected from $R_5$, X is —C(Z)—, or —C(Z)$C_{1-4}$alkyl- where —C(Z) is the point of attachment to the imidazole ring, and Ar is phenyl, 1-naphthyl, 2-naphthyl, or pyridyl, and Ar is unsubstituted or substituted with one, two, or three substituents each of which is independently selected from the group consisting of
  (1) $C_{1-10}$ alkyl,
  (2) $R_5$,
  (3) $C_{1-10}$ alkyl substituted with up to 5 groups independently selected from $R_5$,
  (4) phenyl, optionally substituted with up to 5 groups independently selected from $C_{1-10}$ alkyl, $R_5$, and $C_{1-10}$ alkyl substituted with up to 5 groups independently selected from $R_5$,
  (5) 1-naphthyl, optionally substituted with up to 5 groups independently selected from $C_{1-10}$ alkyl, $R_5$, and $C_{1-10}$ alkyl substituted with up to 5 groups independently selected from $R_5$,
  (6) 2-naphthyl, optionally substituted with up to 5 groups independently selected from $C_{1-10}$ alkyl, $R_5$, and $C_{1-10}$ alkyl substituted with up to 5 groups independently selected from $R_5$,
  (7) pyridyl, optionally substituted with up to 5 groups independently selected fom $C_{1-10}$ alkyl, $R_5$, and $C_{1-10}$ alkyl substituted with up to 5 groups independently selected from $R_5$, $R_5$ is
  (1) —$OR_8$,
  (2) —$NO_2$,
  (3) halogen
  (4) —$S(O)_mR_{11}$,
  (5) —$SR_8$,
  (6) —$S(O)_mOR_8$,
  (7) —$S(O)_mNR_8R_9$,
  (8) —$NR_8R_9$,
  (9) —$O(CR_{10}R_{20})_pNR_8R_9$,
  (10) —$C(O)R_8$,
  (11) —$CO_2R_8$,
  (12) —$CO_2(CR_{10}R_{20})_nCONR_8R_9$,
  (13) —$ZC(O)R_8$,
  (14) —CN,

(15) —C(Z)NR$_8$R$_9$,
(16) NR$_{10}$C(Z)R$_8$,
(17) —C(Z)NR$_8$OR$_9$,
(18) NR$_{10}$C(Z)NR$_8$R$_9$,
(19) —NR$_{10}$S(O)$_m$R$_{11}$,
(20) —C(=NOR$_{21}$)R$_8$,
(21) —NR$_{10}$C(=NR$_{15}$)SR$_{11}$,
(22) —NR$_{10}$C(=NR$_{15}$)NR$_8$R$_9$,
(23) —NR$_{10}$C(=CR$_{14}$R$_{24}$)SR$_{11}$,
(24) —NR$_{10}$C(=CR$_{14}$R$_{24}$)NR$_8$R$_9$,
(25) —NR$_{10}$C(O)C(O)NR$_8$R$_9$,
(26) —NR$_{10}$C(O)C(O)OR$_{10}$,
(27) —C(=NR$_{13}$)NR$_8$R$_9$,
(28) —C(=NOR$_{13}$)NR$_8$R$_9$,
(29) —C(=NR$_{13}$)ZR$_{11}$,
(30) —OC(Z)NR$_8$R$_9$,
(31) —NR$_{10}$S(O)$_m$CF$_3$, or
(32) —NR$_{10}$C(Z)OR$_{10}$.

R$_8$ and R$_9$ are independently selected from,
(1) hydrogen, and
(2) R$_{11}$; or R$_{10}$ and R$_{20}$ is each independently selected from hydrogen and C$_{1-4}$ alkyl;

R$_{11}$ is
(1) C$_{1-10}$ alkyl,
(2) halo-substituted C$_{1-10}$ alkyl,
(3) C$_{2-10}$ alkenyl,
(4) C$_{2-10}$ alkynyl,
(5) C$_{3-7}$ cycloalkyl,
(6) C$_{5-7}$ cycloalkenyl,
(7) aryl, optionally substituted with OR$_{10}$,
(8) arylalkyl, wherein the aryl portion is optionally substituted with OR$_{10}$,
(9) pyridyl or
(10) pyridyl alkyl;

R$_{12}$ is
(1) hydrogen,
(2) —C(Z)R$_{13}$,
(3) optionally substituted C$_{1-4}$ alkyl, wherein the substituents may be halo, C$_{1-3}$ alkoxy, amino, or carboxy,
(4) optionally substituted aryl C$_{1-4}$ alkyl, wherein the substituents may be halo, C$_{1-3}$ alkoxy, amino, or carboxy, or
(5) S(O)$_2$R$_{25}$;

R$_{13}$ is
(1) hydrogen, or
(2) R$_{25}$;

R$_{14}$ and R$_{24}$ is each independently selected from
(1) hydrogen,
(2) C$_{1-4}$ alkyl,
(3) nitro and
(4) cyano;

R$_{15}$ is
(1) hydrogen,
(2) cyano,
(3) C$_{1-4}$ alkyl,
(4) C$_{3-7}$ cycloalkyl or
(5) aryl;

R$_{21}$ is
(1) R$_{13}$,
(2) a pharmaceutically acceptable cation, or
(3) aroyl, or
(4) C$_{1-10}$ alkanoyl;

R$_{25}$ is
(1) C$_{1-10}$ alkyl,
(2) C$_{3-7}$ cycloalkyl,
(3) pyridyl C$_{1-10}$ alkyl,
(4) aryl,
(5) aryl C$_{1-10}$ alkyl, or
(6) pyridyl;

Z is oxygen or sulfur;
m is 1 or 2;
n is 1 to 10;
p is 1 to 10;
a pharmaceutically acceptable salt thereof.

2. A compound of claim 1 wherein R$_2$ is H or —C(Z)OC$_{1-4}$alkyl, and Z is oxygen or sulfur.

3. A compound of claim 1 wherein
R$_3$ is phenyl, 1-naphthyl or 2-naphthyl each of which is unsubstituted or substituted with one, two or three groups each of which is independently selected from the group consisting of
(1) C$_{1-10}$ alkyl,
(2) R$_5$, and
(3) C$_{1-10}$ alkyl substituted with up to 5 groups independently selected from R$_5$.

4. A compound of claim 1 wherein
R$_4$ is —X—Ar wherein
X is a bond and Ar is substituted phenyl, substituted 1-naphthyl, or substituted 2-naphthyl, wherein said substituent is one or two groups each of which is independently selected from the group consisting of
(1) phenyl, optionally substituted with up to 5 groups independently selected from C$_{1-10}$ alkyl, R$_5$, and C$_{1-10}$ alkyl substituted with up to 5 groups independently selected from R$_5$,
(2) 1-naphthyl, optionally substituted with up to 5 groups independently selected from C$_{1-10}$ alkyl, R$_5$, and C$_{1-10}$ alkyl substituted with up to 5 groups independently selected from R$_5$,
(3) 2-naphthyl, optionally substituted with up to 5 groups independently selected from C$_{1-10}$ alkyl, R$_5$, and C$_{1-10}$ alkyl substituted with up to 5 groups independently selected from R$_5$,
(4) pyridyl, optionally substituted with up to 5 groups independently selected from C$_{1-10}$ alkyl, R$_5$, and C$_{1-10}$ alkyl substituted with up to 5 groups independently selected from R$_5$, or
X is —C(Z)— and Ar is phenyl, 1-naphthyl, 2-naphthyl, or pyridyl, and Ar is unsubstituted or substituted with one, two, or three substituents each of which is independently selected from the group consisting of
(1) C$_{1-10}$ alkyl,
(2) R$_5$,
(3) C$_{1-10}$ alkyl substituted with up to 5 groups independently selected from R$_5$,
(4) phenyl, optionally substituted with up to 5 groups independently selected from C$_{1-10}$ alkyl, R$_5$, and C$_{1-10}$ alkyl substituted with up to 5 groups independently selected from R$_5$,
(5) 1-naphthyl, optionally substituted with up to 5 groups independently selected from C$_{1-10}$ alkyl, R$_5$, and C$_{1-10}$ alkyl substituted with up to 5 groups independently selected from $R_5$, (6) 2-naphthyl, optionally substituted with up to 5 groups independently selected from $C_{1-10}$ alkyl, $R_5$, and $C_{1-10}$ alkyl substituted with up to 5 groups independently selected from $R_5$, (7) pyridyl, optionally substituted with up to 5 groups independently selected from $C_{1-10}$ alkyl, $R_5$, and $C_{1-10}$ alkyl substituted with up to 5 groups independently selected from $R_5$.

5. A compound of claim 1 wherein $R_1$ is 4-pyridyl;

$R_2$ is hydrogen or —C(Z)O$C_{1-4}$alkyl;

$R_3$ is phenyl, 1-naphthyl, 2-naphthyl or pyridyl each of which is unsubstituted or substituted with one, two or three substituents each of which is independently selected from the group consisting of
- (1) $C_{1-10}$ alkyl,
- (2) $R_5$, and
- (3) $C_{1-10}$ alkyl substituted with up to 5 groups independently selected from $R_5$;

$R_4$ is —X—Ar wherein

X is a bond and Ar is substituted phenyl, substituted 1-naphthyl, or substituted 2-naphthyl, wherein said substituent is one or two groups each of which is independently selected from the group consisting of (1) phenyl, optionally substituted with up to 5 groups independently selected from $C_{1-10}$ alkyl, $R_5$, and $C_{1-10}$ alkyl substituted with up to 5 groups independently selected from $R_5$, (2) 1-naphthyl, optionally substituted with up to 5 groups independently selected from $C_{1-10}$ alkyl, $R_5$, and $C_{1-10}$ alkyl substituted with up to 5 groups independently selected from $R_5$, (3) 2-naphthyl, optionally substituted with up to 5 groups independently selected from $C_{1-10}$ alkyl, $R_5$, and $C_{1-10}$ alkyl substituted with up to 5 groups independently selected from $R_5$, (4) pyridyl, optionally substituted with up to 5 groups independently selected from $C_{1-10}$ alkyl, $R_5$, and $C_{1-10}$ alkyl substituted with up to 5 groups independently selected from $R_5$, or X is —C(Z)—, and Ar is phenyl, 1-naphthyl, 2-naphthyl, or pyridyl, and Ar is unsubstituted or substituted with one, two, or three substituents each of which is independently selected from the group consisting of (1) $C_{1-10}$ alkyl,
(2) $R_5$,
(3) $C_{1-10}$ alkyl substituted with up to 5 groups independently selected from $R_5$,
(4) phenyl, optionally substituted with up to 5 groups independently selected from $C_{1-10}$ alkyl, $R_5$, and $C_{1-10}$ alkyl substituted with up to 5 groups independently selected from $R_5$,
(5) 1-naphthyl, optionally substituted with up to 5 groups independently selected from $C_{1-10}$ alkyl, $R_5$, and $C_{1-10}$ alkyl substituted with up to 5 groups independently selected from $R_5$,
(6) 2-naphthyl, optionally substituted with up to 5 groups independently selected from $C_{1-10}$ alkyl, $R_5$, and $C_{1-10}$ alkyl substituted with up to 5 groups independently selected from $R_5$,
(7) pyridyl, optionally substituted with up to 5 groups independently selected from $C_{1-10}$ alkyl, $R_5$, and $C_{1-10}$ alkyl substituted with up to 5 groups independently selected from $R_5$, $R_5$ is
- (1) —$OR_8$,
- (2) halogen
- (3) —$SR_8$, or $R_8$ is selected from
- (1) hydrogen,
- (2) $R_{11}$;

$R_{10}$ and $R_{20}$ is each independently selected from hydrogen and $C_{1-4}$ alkyl;

$R_{11}$ is
- (1) $C_{1-10}$ alkyl
- (2) halo-substituted $C_{1-10}$ alkyl,
- (3) $C_{3-7}$ cycloalkyl,
- (4) aryl, optionally substituted with $OR_{10}$, or
- (5) arylalkyl, wherein the aryl portion is optionally substituted with $OR_{10}$;

Z is oxygen or sulfur;

a pharmaceutically acceptable salt thereof.

6. A compound of claim 1 wherein $R_1$ is 4-pyridyl;

$R_2$ is hydrogen or —C(Z)O$C_{1-4}$alkyl;

$R_3$ is phenyl, 1-naphthyl or 2-naphthyl each of which is unsubstituted or substituted with one, two or three substituents each of which is independently selected from the group consisting of
- (1) halogen, and
- (2) $OR_8$;

$R_4$ is —X—Ar wherein

X is a bond and Ar is substituted phenyl, substituted 1-naphthyl, or substituted 2-naphthyl, wherein said substituent is one or two groups each of which is independently selected from the group consisting of (1) phenyl, optionally substituted with up to 5 groups independently selected from $C_{1-10}$ alkyl, $R_5$, and $C_{1-10}$ alkyl substituted with up to 5 groups independently selected from $R_5$, (2) 1-naphthyl, optionally substituted with up to 5 groups independently selected from $C_{1-10}$ alkyl, $R_5$, and $C_{1-10}$ alkyl substituted with up to 5 groups independently selected from $R_5$, (3) 2-naphthyl, optionally substituted with up to 5 groups independently selected from $C_{1-10}$ alkyl, $R_5$, and $C_{1-10}$ alkyl substituted with up to 5 groups independently selected from $R_5$, (4) pyridyl, optionally substituted with up to 5 groups independently selected from $C_{1-10}$ alkyl, $R_5$, and $C_{1-10}$ alkyl substituted with up to 5 groups independently selected from $R_5$;

X is —C(Z)—, and Ar is phenyl, 1-naphthyl, 2-naphthyl, or pyridyl, and Ar is unsubstituted or substituted with one, two, or three substituents each of which is independently selected from the group consisting of (1) $C_{1-10}$ alkyl,
(2) $R_5$,
(3) $C_{1-10}$ alkyl substituted with up to 5 groups independently selected from $R_5$,
(4) phenyl, optionally substituted with up to 5 groups independently selected from $C_{1-10}$ alkyl, $R_5$, and $C_{1-10}$ alkyl substituted with up to 5 groups independently selected from $R_5$,
(5) 1-naphthyl, optionally substituted with up to 5 groups independently selected from $C_{1-10}$ alkyl, $R_5$, and $C_{1-10}$ alkyl substituted with up to 5 groups independently selected from $R_5$, (6) 2-naphthyl, optionally substituted with up to 5 groups independently selected from $C_{1-10}$ alkyl, $R_5$, and $C_{1-10}$ alkyl substituted with up to 5 groups independently selected from $R_5$, (7) pyridyl, optionally substituted with up to 5 groups independently selected from $C_{1-10}$ alkyl, $R_5$, and $C_{1-10}$ alkyl substituted with up to 5 groups independently selected from $R_5$, $R_5$ is (1) —$OR_8$, (2) halogen, or (3) —$SR_8$;

$R_8$ is selected from (1) hydrogen, (2) $R_{11}$; or $R_{10}$ and $R_{20}$ is each independently selected from hydrogen and $C_{1-4}$ alkyl;

$R_{11}$ is (1) $C_{1-10}$ alkyl, (2) halo-substituted $C_{1-10}$ alkyl, (3) $C_{3-7}$ cycloalkyl, (4) aryl, optionally substituted with $OR_{10}$, or (5) arylalkyl, wherein the aryl portion is optionally substituted with $OR_{10}$;

Z is oxygen or sulfur;

a pharmaceutically acceptable salt thereof.

7. A compound of claim 1 selected from the group consisting of:

(3) 4-(4-biphenyl)-2-(4-chlorophenyl)-5-(4-pyridyl) imidazole, (4) 4-(4-biphenyl)-2-(3-chlorophenyl)-5-(4-pyridyl) imidazole, (5) 2-(4-chlorophenyl)-4-(4'-ethyl-4-biphenyl)-5-(4-pyridyl)imidazole, (6) 2-(3-chlorophenyl)-4-(4'-ethyl-4-biphenyl)-5-(4-pyridyl)imidazole, (7) 2-(4-chlorophenyl)-4-(4-(1-naphthyl)phenyl)-5-(4-pyridyl)imidazole, (8) 2-(4-chlorophenyl)-4-(3'-methoxy-4-biphenyl)-5-(4-pyridyl)imidazole, (9) 2-(4-chlorophenyl)-4-(3'-methoxy-4-biphenyl)-5-(4-pyridyl)imidazole,

(10) 2-(4-chlorophenyl)-4-(2'-methoxy-4-biphenyl)-5-(4-pyridyl)imidazole,

(12) 2-(4-chlorophenyl)-4-(4'-methoxy-3-biphenyl)-5-(4-pyridyl)imidazole,

(13) 2-(4-chlorophenyl)-4-(3'-methoxy-3-biphenyl)-5-(4-pyridyl)imidazole,

(14) 2-(4-chlorophenyl)-4-(4'-(4-methoxybenzylthio)-4-biphenyl)-5-(4-pyridyl)imidazole,

(15) 4-(3-biphenyl)-2-(4-chlorophenyl)-5-(4-pyridyl) imidazole,

(16) 2-(4-chlorophenyl)-4-(2'-methoxy-3-biphenyl)-5-(4-pyridyl)imidazole,

(17) 2-(4-chlorophenyl)-4-(3-(1-naphthyl)phenyl)-5-(4-pyridyl)imidazole,

(18) 2-(4-chlorophenyl)-4-(2',4'-dichloro-3-biphenyl)-5-(4-pyridyl)imidazole,

(19) 2-(4-chlorophenyl)-4-(3-(2-naphthyl)phenyl)-5-(4-pyridyl)imidazole,

(20) 2-(4-chlorophenyl)-4-(4'-chloro-3-biphenyl)-5-(4-pyridyl)imidazole,

(21) 2-(4-chlorophenyl)-4-(3'-chloro-3-biphenyl)-5-(4-pyridyl)imidazole,

(22) 2-(4-chlorophenyl)-4-(3',5'-dichloro-3-biphenyl)-5-(4-pyridyl)imidazole,

(23) 2-(4-chlorophenyl)-4-(4'-(4-methoxybenzylthio)-3-biphenyl)-5-(4-pyridyl)imidazole,

(26) 2-(4-chlorophenyl)-4-(2',4-dimethoxy-3-biphenyl)-5-(4-pyridyl)imidazole,

(29) 2-(4-chlorophenyl)-4-benzoyl-5-(4-pyridyl) imidazole.

8. A compound of claim 6 wherein $R_4$ is X—Ar and wherein

X is a bond and Ar is substituted phenyl, substituted 1-naphthyl, or substituted 2-naphthyl, wherein said substituent is one or two groups each of which is independently selected from the group consisting of (1) phenyl, optionally substituted with up to 5 groups independently selected from $C_{1-10}$ alkyl, $R_5$, and $C_{1-10}$ alkyl substituted with up to 5 groups independently selected from $R_5$, (2) 1-naphthyl, optionally substituted with up to 5 groups independently selected from $C_{1-10}$ alkyl, $R_5$, and $C_{1-10}$ alkyl substituted with up to 5 groups independently selected from $R_5$, (3) 2-naphthyl, optionally substituted with up to 5 groups independently selected from $C_{1-10}$ alkyl, $R_5$, and $C_{1-10}$ alkyl substituted with up to 5 groups independently selected from $R_5$, (4) pyridyl, optionally substituted with up to 5 groups independently selected from $C_{1-10}$ alkyl, $R_5$, and $C_{1-10}$ alkyl substituted with up to 5 groups independently selected from $R_5$.

9. The compound of 2-(4-chlorophenyl)-4-(2-biphenyl) methyl-5-(4-pyridyl) imidazole.

10. A pharmaceutical composition comprising a compound according to claim 1 and a pharmaceutically acceptable carrier.

* * * * *